US012746342B2

United States Patent

(12) United States Patent
Nagar
(10) Patent No.: US 12,746,342 B2
(45) Date of Patent: Sep. 29, 2026

(54) APPARATUSES, SYSTEMS AND METHODS FOR STORING A SUBSTANCE

(71) Applicant: Ron Nagar, Tel Aviv (IL)

(72) Inventor: Ron Nagar, Tel Aviv (IL)

(73) Assignee: TempraMed Israel, Ltd., Tel Aviv (IL)

( * ) Notice: Subject to any disclaimer, the term of this patent is extended or adjusted under 35 U.S.C. 154(b) by 508 days.

(21) Appl. No.: 18/264,059

(22) PCT Filed: Feb. 2, 2022

(86) PCT No.: PCT/IB2022/000051
§ 371 (c)(1),
(2) Date: Aug. 2, 2023

(87) PCT Pub. No.: WO2022/167865
PCT Pub. Date: Aug. 11, 2022

(65) Prior Publication Data

US 2024/0091458 A1 Mar. 21, 2024

Related U.S. Application Data

(60) Provisional application No. 63/144,652, filed on Feb. 2, 2021.

(51) Int. Cl.
*A61M 5/32* (2006.01)
*B65D 81/38* (2006.01)

(52) U.S. Cl.
CPC ....... *A61M 5/3202* (2013.01); *B65D 81/3876* (2013.01); *A61M 2205/3368* (2013.01)

(58) Field of Classification Search
CPC ...... A61M 5/3202; A61M 5/002; A61J 1/165; A61J 2200/72; A61J 2200/50;
(Continued)

(56) References Cited

U.S. PATENT DOCUMENTS 3,802,220 A 4/1974 Pompo
3,893,834 A 7/1975 Armstrong
(Continued)

FOREIGN PATENT DOCUMENTS

CN 101208568 A 6/2008
CN 108027192 A 5/2018
(Continued)

OTHER PUBLICATIONS

Extended European Search Report for Application No. EP 19875793.2, mailed on Oct. 14, 2022, 11 pages.
(Continued)

*Primary Examiner* — Katrina M Stransky
(74) *Attorney, Agent, or Firm* — Fenwick & West LLP

(57) ABSTRACT

A substance storage apparatus for storing a substance-container configured with an outer surface formed of a first material and for containing a substance, the apparatus comprising a housing formed of a base at a distal end of the storage apparatus and a lateral wall longitudinally extending therefrom to a top portion at a proximal end, the top portion comprising a cover at least a portion of which is formed of a second material including a greater degree of resilience than the first material and an aperture at least partially surrounded by the cover and configured for receiving an end of the substance-container therethrough; a thermal insulation element disposed within the housing and configured to provide a thermal shield to the substance; a receptacle having a size and shape configured for receiving the substance-container therein; and a phase change material (PCM) element configured to thermally regulate the temperature of the substance.

21 Claims, 19 Drawing Sheets

(58) Field of Classification Search
CPC .. A61J 1/2096; A61J 2200/40; A61J 2200/42; A61J 2200/44; A61J 2200/70
See application file for complete search history.

(56) References Cited

U.S. PATENT DOCUMENTS

| | | | | |
|---|---|---|---|---|
| 3,980,083 | A | 9/1976 | Elliott | |
| 4,373,535 | A | 2/1983 | Martell | |
| 4,619,678 | A | 10/1986 | Rubin | |
| 4,723,974 | A | 2/1988 | Ammerman | |
| 4,924,935 | A | 5/1990 | Van Winckel | |
| 5,603,220 | A | 2/1997 | Seaman | |
| 5,695,090 | A | 12/1997 | Burdick | |
| 6,454,746 | B1 | 9/2002 | Bydlon et al. | |
| 7,240,513 | B1 | 7/2007 | Conforti | |
| 7,861,538 | B2 | 1/2011 | Welle et al. | |
| 8,061,149 | B1 | 11/2011 | Gowans et al. | |
| 8,398,602 | B2 | 3/2013 | Ilo et al. | |
| 8,646,282 | B2 | 2/2014 | Ilercil et al. | |
| 8,663,167 | B2 | 3/2014 | Bartha | |
| 8,887,512 | B2 | 11/2014 | Olsen et al. | |
| 9,447,995 | B2 | 9/2016 | Bloedow et al. | |
| 9,581,384 | B1 | 2/2017 | Scofield et al. | |
| 9,791,184 | B2 | 10/2017 | Novisoff et al. | |
| 10,254,499 | B1 | 4/2019 | Cohen et al. | |
| 10,973,996 | B2 | 4/2021 | Nagar | |
| 11,499,770 | B2 | 11/2022 | Rizzo et al. | |
| 11,857,495 | B2 | 1/2024 | Nagar | |
| 11,992,459 | B2 | 5/2024 | Nagar | |
| 12,398,937 | B2 | 8/2025 | Nagar | |
| 12,533,296 | B2 | 1/2026 | Nagar | |
| 2001/0048985 | A1 | 12/2001 | Legare | |
| 2002/0000443 | A1 | 1/2002 | Hunter | |
| 2003/0128898 | A1 | 7/2003 | Malone et al. | |
| 2006/0191282 | A1 | 8/2006 | Sekiya et al. | |
| 2006/0271014 | A1 | 11/2006 | Hynes et al. | |
| 2006/0276768 | A1 | 12/2006 | Miller et al. | |
| 2008/0022696 | A1 | 1/2008 | Welle et al. | |
| 2008/0264261 | A1 | 10/2008 | Kavazov et al. | |
| 2008/0269687 | A1 | 10/2008 | Chong et al. | |
| 2009/0049845 | A1 | 2/2009 | McStravick et al. | |
| 2009/0139248 | A1 | 6/2009 | Crumlin et al. | |
| 2009/0301511 | A1 | 12/2009 | Vinci | |
| 2010/0314397 | A1 | 12/2010 | Williams et al. | |
| 2011/0155621 | A1 | 6/2011 | Lindquist et al. | |
| 2011/0218502 | A1 | 9/2011 | Iio et al. | |
| 2012/0312031 | A1 | 12/2012 | Olsen et al. | |
| 2013/0221013 | A1 | 8/2013 | Kolowich et al. | |
| 2013/0255306 | A1 | 10/2013 | Mayer | |
| 2014/0090737 | A1 | 4/2014 | Reid | |
| 2014/0165607 | A1 | 6/2014 | Alexander | |
| 2014/0216485 | A1 | 8/2014 | Egoyants et al. | |
| 2014/0263368 | A1 | 9/2014 | Booska | |
| 2014/0343493 | A1 | 11/2014 | Wengreen | |
| 2015/0151893 | A1 | 6/2015 | Wengreen et al. | |
| 2015/0229267 | A1 | 8/2015 | Hilliard | |
| 2015/0239640 | A1 | 8/2015 | Smith et al. | |
| 2016/0311585 | A1* | 10/2016 | Rideg | B65D 47/2031 |
| 2017/0241702 | A1 | 8/2017 | Klett et al. | |
| 2018/0036202 | A1* | 2/2018 | Wengreen | A61M 5/002 |
| 2018/0207368 | A1* | 7/2018 | Nagar | A61J 1/16 |
| 2018/0283761 | A1 | 10/2018 | Büttiker | |
| 2018/0328644 | A1 | 11/2018 | Rizzo et al. | |
| 2018/0333330 | A1* | 11/2018 | Nagar | A61M 5/24 |
| 2019/0226744 | A1 | 7/2019 | Wood et al. | |
| 2019/0285328 | A1 | 9/2019 | Emond et al. | |
| 2020/0171291 | A1 | 6/2020 | Snyder | |
| 2021/0228820 | A1 | 7/2021 | Nagar | |
| 2021/0396446 | A1 | 12/2021 | Nagar | |
| 2024/0342057 | A1 | 10/2024 | Nagar | |
| 2025/0090422 | A1 | 3/2025 | Nagar | |
| 2026/0126232 | A1 | 5/2026 | Nagar | |

FOREIGN PATENT DOCUMENTS

| | | | |
|---|---|---|---|
| CN | 209209482 | U | 8/2019 |
| EP | 2361203 | A1 | 8/2011 |
| EP | 3610842 | A1 | 2/2020 |
| FR | 2635580 | A1 | 2/1990 |
| GB | 2176711 | A | 1/1987 |
| GB | 2422657 | A | 8/2006 |
| JP | 02115672 | A | 4/1990 |
| JP | 04201877 | A | 7/1992 |
| JP | 3041860 | U | 10/1997 |
| JP | 2002-090019 | A | 3/2002 |
| JP | 2006-200813 | A | 8/2006 |
| JP | 2018-532976 | A | 11/2018 |
| WO | 1999/030092 | A1 | 6/1999 |
| WO | WO-2013034458 | A1 | 3/2013 |
| WO | WO-2014064691 | A2 | 5/2014 |
| WO | WO-2014163120 | A1 | 10/2014 |
| WO | WO-2014192019 | A2 | 12/2014 |
| WO | WO-2015055836 | A1 | 4/2015 |
| WO | 2015/093311 | A1 | 6/2015 |
| WO | WO-2016011207 | A1 | 1/2016 |
| WO | WO-2017055280 | A1 | 4/2017 |
| WO | WO-2017090019 | A2 | 6/2017 |
| WO | WO-2020084543 | A1 | 4/2020 |
| WO | 2022/167865 | A1 | 8/2022 |

OTHER PUBLICATIONS

Extended European Search Report issued on Feb. 21, 2018, for EP Application No. 15822617.5, 7 pages.
Extended European Search Report issued on Jul. 2, 2019, for EP Application No. 16868134.4, 7 pages.
Extended European Search Report issued on Nov. 20, 2019, for EP Application No. 19181060.5, 7 pages.
International Search Report and Written Opinion for International Application No. PCT/IB2022/00051, dated Jun. 30, 2022, 20 pages.
International Search Report and Written Opinion, mailed Oct. 7, 2015, for International Application No. PCT/US2015/040655, 15 pages.
International Search report for Application No. PCT/IL16/00021, dated May 16, 2017, 4 pages.
International Search Report issued in PCT/IB2019/059096, dated Feb. 4, 2020, 3 pages.
Screenshots from Website: www.insulinsafe.com.cn/en/; May 10, 2013; Beijing Insulinsafe Healthcare Limited, 1 page.
Screenshots from Website: www.insulinsafe.com.cn/en/category/product; Sep. 13, 2014; Beijing Science and Technology Co., Ltd, 11 pages.
U.S. Appl. No. 19/361,501, filed Oct. 17, 2025, Inventor Ron Nagar.

* cited by examiner

APPARATUSES, SYSTEMS AND METHODS FOR STORING A SUBSTANCE

RELATED APPLICATIONS

The present application is a 35 U.S.C. § 371 national stage entry of PCT/IB2022/000051, filed Feb. 2, 2022, titled the same, which claims benefit of and priority to, and the benefit of, U.S. Provisional Patent Application No. 63/144,652, filed on Feb. 2, 2021 titled: "Devices, Systems and Methods for Controlling and Maintaining Conditions of Substances". Each of the foregoing disclosures is herein incorporated by reference its entirety.

TECHNICAL FIELD

Some embodiments of the present disclosure generally relate to apparatuses for storing a substance.

BACKGROUND

Drugs and other substances can be sensitive to environmental conditions such as light, humidity, temperature, atmosphere, pressure and other conditions. Many drugs and other substances have limited boundaries to such conditions that if exceeded, can degrade the drug efficacy or degrade the substance.

Additionally, users receive drugs at the pharmacy and must carry these drugs to their home. When these drugs have to be kept refrigerated, users have trouble making sure that the volume of drug is refrigerated during transport to their domestic refrigerator. While they use icepacks, these icepacks do not come in contact with the drug and as a result do not assure that the drug is at proper refrigeration temperature. In some cases, should the ice packs make direct contact with the drug it might freeze, causing the drug to degrade.

While apparatuses exist that can maintain drugs and substance containers, such as drug-containing delivery devices, under controlled environmental conditions, such current apparatuses are quite large and typically require a regular AC power supply for their operation, or large batteries of limited duration. Other devices, such as cooling packs, require large amounts of cooling material (ice or water evaporation) to maintain a case under cooled temperatures.

SUMMARY OF SOME OF THE EMBODIMENTS

In some embodiments of the present disclosure, the environmental conditions of any substance may be controlled. The environmental condition (which may be referred to as "condition" herein) may include temperature, light, humidity, atmosphere, pressure or any other condition affecting the substance.

The substance may comprise any material affected by the condition or any type of substance.

In a non-limiting example, the substance may comprise a drug, a pharmaceutical, a biological substance, such as hormones, a growth hormone, blood, enzymes, body fluids, body parts, body organs, body tissue, sperms, or eggs. The substance may comprise analyte indicators, analyte sensors and/or analyte detectors comprising any type of material. The analyte indicator or sensor may comprise for example, a blood glucose test strip or blood glucose sensitive materials, configured for indicating the blood glucose level. The blood glucose strip may comprise enzymes or any other biological material. In another example, the analyte indicator or sensor may comprise urine test strips. The analyte indicator or sensor may comprise any diagnostic tool based on a biological indicator comprising a biological and/or chemical material.

The substance may comprise cosmetics, such as lipsticks, perfumes, toiletries, hair or skin care products, sprays, mousses, emulsions and gels, for example. The substance may comprise, resins, adhesives, glues, epoxy or cyanoacrylate glue, for example.

Any of the mentioned substances may include any suitable form, such as a solid, liquid, emulsion, gas, gel, granules, and powder or a combination thereof, for example. The substance may include more than one substance at the same or different state or phase, such as, for example, a liquid mixed with another liquid or a liquid mixed with a powder. In some embodiments, keeping one part of the mixture at a particular environmental condition requires a smaller amount of power than both parts. For example, a substance in a powder state is of smaller volume than the same substance in its liquid state. Therefore, maintaining a small amount of powder at a specific temperature requires less power than maintaining larger amount of liquids at the specific temperature.

In some embodiments, the substance may be contained within a container.

In some embodiments, the container may comprise a substance storage device or a substance delivery device. The container may be configured in any suitable configuration for containing a substance therein. In some examples the container may comprise a device for drug injection delivery such as an injection pen, a jet injector and/or a syringe. Some further non-limiting exemplary containers for containing substances may include a substance vial, a substance cartridge, an ampoule, a substance pump, a pill box, a capsule container, an inhalator, a substance spraying device, an infusion device with a pump or an infusion device without a pump. In some embodiments, the container may comprise a box. In some embodiments, the container may comprise a container for storing and transferring blood glucose strips or any other analyte, e.g. a biologic or chemical analyte monitoring strips.

In accordance with some embodiments of the present application there is provided a substance storage apparatus for storing a substance contained is a substance container.

In an embodiment there is provided a substance storage apparatus for storing a substance-container configured with an outer surface formed of a first material and for containing a substance, the apparatus comprising a housing formed of a base at a distal end of the storage apparatus and a lateral wall longitudinally extending therefrom to a top portion at a proximal end, the top portion comprising a cover at least a portion of which is formed of a second material including a greater degree of resilience than the first material and an aperture at least partially surrounded by the cover and configured for receiving an end of the substance-container therethrough; a thermal insulation element disposed within the housing and configured to provide a thermal shield to the substance; a receptacle having a size and shape configured for receiving the substance-container therein; and a phase change material (PCM) element configured to thermally regulate the temperature of the substance.

In some embodiments, top portion further comprises at least one recess extending from the aperture. In some embodiments, the at least one recess comprises two or more recesses. In some embodiments, the aperture is centrally positioned at the top portion, and wherein the top portion further comprises two or more equidistant recesses extending from the aperture. In some embodiments, the at least one recess is selected from the group consisting of a slit, an orifice, an opening and a combination thereof.

In some embodiments, the cover comprises a plurality of flaps or leaflets. In some embodiments, the flaps or leaflets are arranged so as to form a tricuspid valve-like shape. In some embodiments, the receptacle is formed with a peripheral wall defining therein a lumen, the lumen configured with a predetermined diameter dimensioned to receive a reservoir region of the substance-container containing the substance therein, and the aperture is configured with a diameter either equal to or less than the predetermined lumen diameter.

In some embodiments, a diameter of the aperture is sized to accommodate different types of cylindrical substance-containers, each substance-container including a different diameter. In some embodiments, the at least a portion of the cover is configured for gripping the outer surface of the substance-container so as to secure the substance-container within the receptacle. In some embodiments, a peripheral wall of the receptacle comprises an internal surface including a shape complementary to a shape of the substance-container for securely receiving the substance-container with minimal or no gaps between the internal surface and the peripheral wall of the substance container. In some embodiments, the receptacle comprises an external surface and the PCM volume is defined between the external surface and an inner wall of the thermal insulation element, and the PCM element is disposed within the PCM volume.

In some embodiments, the PCM volume contains the PCM element with minimal or no air gaps therein. In some embodiments, the PCM element is inserted into the PCM volume in an at least partially liquid state. In some embodiments, the PCM element is initially in an at least partially liquid state during assembly of the apparatus, such that it is poured into an inner wall of the thermal insulation element prior to insertion of the receptacle in the apparatus. In some embodiments, during assembly of the apparatus, the PCM element is assembled in the apparatus in an at least partially liquid state, such that, the PCM element is poured into the inner wall of the thermal insulation element prior to insertion of the receptacle in the apparatus.

In some embodiments, during assembly of the apparatus, the receptacle is inserted in the PCM element, such that the PCM element fills the PCM volume.

In some embodiments, the PCM element is contiguous with at least a portion of the external wall of the receptacle. In some embodiments, the receptacle comprises at least one lateral projection protruding from an external wall of the receptacle, the at least one lateral projection configured for positioning the receptacle within the PCM volume.

In some embodiments, the at least one lateral projection comprises two or more lateral projections. In some embodiments, the at least one lateral projection is formed of a material with a degree of thermal conductivity equal to or greater than the degree of thermal conductivity of the PCM element. In some embodiments, the apparatus further comprises a sealing element disposed in proximity to the top portion. In some embodiments, the receptacle comprises at least a pair of peripheral protrusions defining a groove therebetween, the groove configured for housing the sealing element.

In some embodiments, the apparatus further comprises at least one of a battery, a processor and electronics for powering at least one of an indicator and a sensor of the apparatus. The least one of the battery, processor and electronics are disposed intermediate the base portion of the housing and a base portion of the thermal insulation element. The thermal insulation element comprises: an external cylinder formed with an external base portion and an external peripheral wall extending longitudinally from the external base portion to a first lip thereof; an internal cylinder formed with an internal base portion and an internal peripheral wall extending longitudinally from the internal base portion to a second lip; and a rim connecting the first lip to the second lip, In some embodiments, the external cylinder, the internal cylinder and rim are configured to enclose the thermal insulation element and define an enclosed chamber intermediate the external cylinder and the internal cylinder, wherein the chamber is evacuated. In some embodiments, the thermal insulation element is enclosed at a distal end thereof by a base portion and is configured with an opening at a proximal end thereof.

In some embodiments, the lateral wall of the housing is formed with at least one flat surface configured to prevent rolling of the substance storage apparatus on a substantially flat surface. In some embodiments, the apparatus further comprises a connecting member configured for connecting the housing to a cap assembly. In some embodiments, the receptacle is sized and shaped so as to fully enclose the substance-container, and wherein the apparatus comprises a lid disposed at the proximal end of the housing.

In some embodiments, wherein the substance-container comprises a substance-injection device configured with a substance reservoir region disposed along a longitudinal axis thereof, intermediate to a plunger region positioned at a first end thereof, and a needle-containing region positioned at a second end thereof.

In some embodiments, the receptacle is configured with a length along its longitudinal axis dimensioned to receive the needle-containing region and the reservoir region of the substance-injection device such that at least a portion of the plunger region protrudes from the top portion. In some embodiments, the substance-injection device includes: a first container portion substantially perpendicular to the longitudinal axis and disposed at the reservoir region, the first container portion configured with a first diameter; and a second container portion substantially parallel to the first container portion and disposed at the needle-containing region, the second container portion configured with a second diameter smaller than the first diameter, wherein the receptacle is shaped complementary to the shape of the substance-injection device, and comprises: a reservoir region-receiving portion configured with a first receptacle-portion including a first diameter and being dimensioned to receive the reservoir region; and a needle-containing region-receiving portion configured with a second receptacle portion including a second diameter and being dimensioned to receive the needle-containing region, wherein the second diameter of the second receptacle portion is smaller than the first diameter of the first receptacle portion.

In some embodiments, the receptacle comprises: a reservoir region-receiving portion dimensioned to snugly receive the reservoir region; and a needle-containing region-receiving portion dimensioned to snugly receive the needle-containing region.

In some embodiments, the apparatus further comprises a temperature sensor configured to measure the temperature of the substance, wherein the substance is operable to be contained in the substance-container within a substance reservoir region and the receptacle comprises a substance reservoir region receiving-portion for receiving the reservoir region, and the temperature sensor is positioned in proximity to the reservoir receiving-portion.

In some embodiments, the receptacle is formed with a protuberance protruding from an internal surface of the receptacle at the reservoir receiving-portion, the protuberance being configured for housing the temperature sensor and positioning the temperature sensor facing the substance reservoir region. In some embodiments, the housing is formed with at least one retainer for preventing the receptacle from being axially displaced in response to expansion of the PCM element within the PCM volume when in an at least partial liquid state.

In some embodiments there is provided, a substance storage apparatus for storing a substance-container configured with a peripheral wall and for containing a substance, the apparatus comprising: a housing formed of a base portion at a distal end of the storage apparatus and a lateral wall longitudinally extending therefrom to a top portion at a proximal end defining an exposed portion exposed to ambient temperatures, a thermal insulation element disposed within the housing and being configured to provide a thermal shield to the substance; a receptacle configured for receiving the substance-container therein; a phase change material element configured to thermally regulate the temperature of the substance, wherein the PCM element is disposed within a PCM volume formed intermediate the receptacle and the thermal insulation element; and at least one thermally conducting element disposed within the PCM volume. In some embodiments the thermally conducting element is configured with a thermal conductivity greater than a thermal conductivity of the PCM element. In some embodiments the thermally conducting element is configured with a thermal conductivity greater than 0.05 Watts/(meter*Kelvin) or more than the thermal conductivity of the PCM element. In some embodiments the thermally conducting element is configured with a thermal conductivity greater than 0.01 Watts/(meter*Kelvin) or more than the thermal conductivity of the PCM element.

In some embodiments the thermally conducting element is configured with a thermal conductivity greater than 10 Watts/(meter*Kelvin) or more than the thermal conductivity of the PCM element. In some embodiments, the thermally conductive element is disposed within the PCM volume at least at a location closer to the distal end of the apparatus than the proximal end of the apparatus. In some embodiments, the thermally conductive element is not disposed within the PCM volume at a location closer to the proximal end of the apparatus than the distal end of the apparatus. In some embodiments the thermally conducting element comprises at least one protrusion protruding from an external surface of the receptacle into the PCM volume. In some embodiments, the at least one protrusion extends axially from the external surface towards the distal end. In some embodiments, the at least one protrusion extends radially from the external surface towards the distal end. In some embodiments the at least one protrusion comprises a plurality of protrusions. In some embodiments, the plurality of protrusions are equidistantly arranged about the external surface. In some embodiments the plurality of protrusions are arranged bisectionally at a distal end of the receptacle. In some embodiments, the thermally conducting element comprises at least two surfaces incontiguous with the receptacle. In some embodiments, the thermally conducting element is disposed in the arranged in the PCM volume incontiguous with the receptacle. In some embodiments, the thermally conducting element comprises a foil at least partially circumscribing an internal surface of the receptacle and at least partially surrounding a reservoir region of the container.

In some embodiments there is provided a substance storage apparatus for storing a substance-container configured with a peripheral wall and for containing a substance, the apparatus comprising: a housing formed of a base portion at a distal end of the storage apparatus and a lateral wall longitudinally extending therefrom to a top portion at a proximal end of the apparatus, a thermal insulation element disposed within the housing and being configured to provide a thermal shield to the substance; a receptacle configured for receiving the substance-container therein; a first phase change material (PCM) element configured to thermally regulate the temperature of the substance, wherein the first PCM element is disposed within a PCM volume formed intermediate the receptacle and the thermal insulation element; and a lid disposed at least partially over the top portion of the housing and comprising a second PCM element. In some embodiments the lid comprises a first portion configured for overlaying the top portion and a second portion extending into the housing when the lid encloses the housing. In some embodiments, the second PCM element is disposed at least within the second portion. In some embodiments, the first portion comprises a thermal insulation element. In some embodiments, the first portion comprises air. In some embodiments, the thermal insulation element of the housing terminates at a lip region thereof, and the second PCM element contained in the second portion is configured to axially extend into the housing towards the distal end, at least beyond the lip region.

In some embodiments, there is provided a substance storage apparatus for storing a substance-container configured with an outer surface formed of a first material and for containing a substance, the apparatus comprising: a housing formed of a base at a distal end of the storage apparatus and a lateral wall longitudinally extending therefrom to a top portion at a proximal end, the top portion comprising: a cover at least a portion of which is formed of a second material including a greater degree of resilience than the first material; and an aperture at least partially surrounded by the cover and configured for receiving an end of the substance-container therethrough.

In some embodiments, there is provided a cap assembly removably couplable to a substance storage apparatus configured for storing a first portion of a substance-container, the cap assembly comprising: a housing extending from the substance storage apparatus at a first end to a top portion at a second end and defining therein a volume for storing a second portion of the substance container; a connector configured for removably connecting the cap assembly to the substance storage apparatus; a human comprehensible interaction unit configured for at least one of receiving and transmitting substance-related information to a user.

In some embodiments, the human comprehensible interaction unit comprises a display displaying to the user at least one of: a time indictive of a duration which passed since a last use of the substance; a temperature of the substance; a capacity of a thermal regulation element disposed within the substance storage apparatus; and a quantity indicative of the quantity of used substance.

In some embodiments, the human comprehensible interaction unit comprises a microphone and/or a speaker.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The principles and operations of the systems, apparatuses and methods according to some embodiments of the present disclosure may be better understood with reference to the drawings, and the following description. The drawings are given for illustrative purposes only and are not meant to be limiting.

DETAILED DESCRIPTION

Figure 1A:
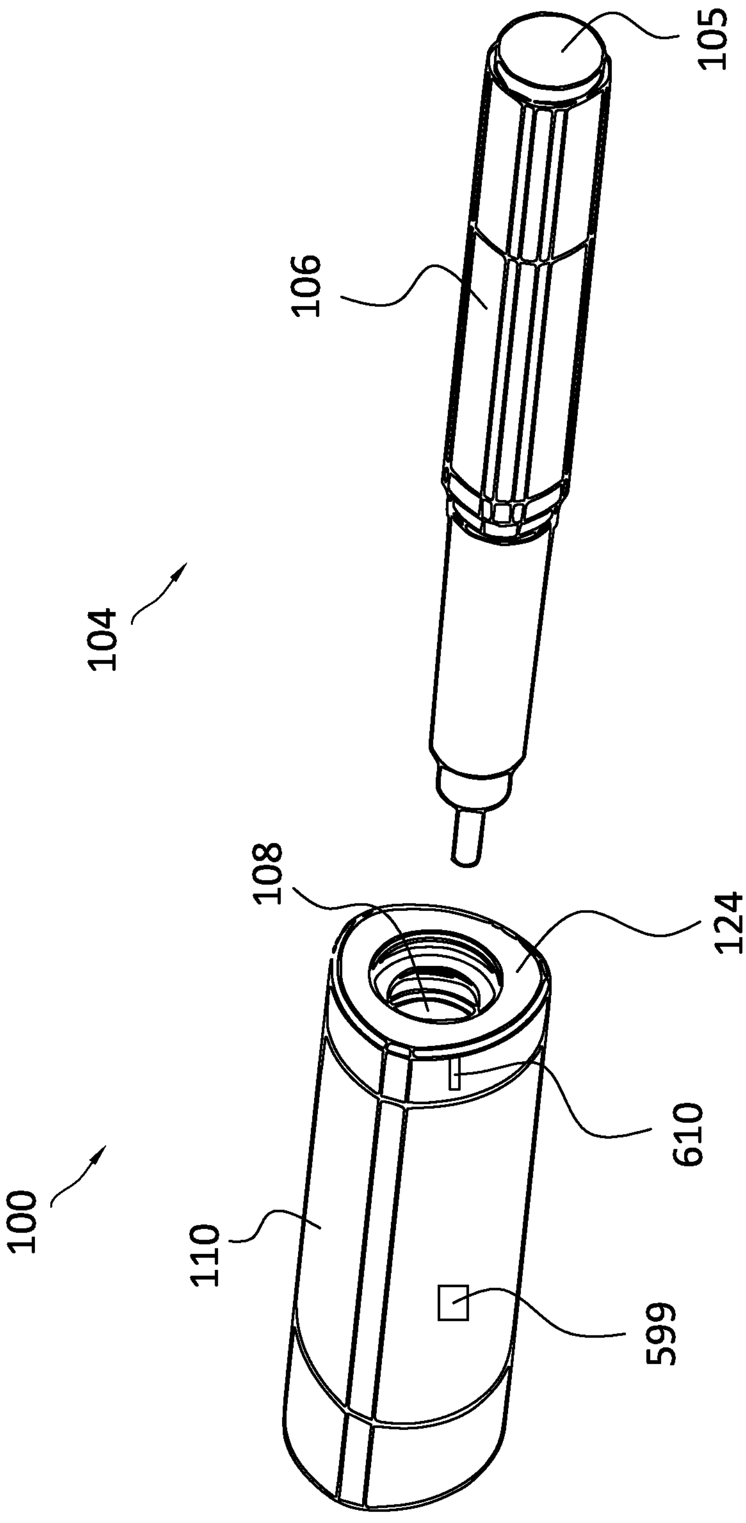
FIGS. 1A-1E are schematic illustrations of an exemplary substance storage apparatus shown with a substance container prior to being inserted in the substance storage apparatus (1A), a sectional view of the substance storage apparatus as shown in FIG. 1A (1B) a sectional view of the substance storage apparatus as shown in FIG. 1A with the substance container inserted therein (1C), a sectional view of the substance storage apparatus of an alternative embodiment of FIG. 1B (1D) and a sectional view of the substance storage apparatus of another alternative embodiment of FIG. 1B (1E), constructed and operative according to some embodiments of the present disclosure.

FIGS. 1A-2B are schematic illustrations of an exemplary substance storage apparatus 100. The substance may comprise in a non-limiting example, a drug, insulin, an anti-allergen, a biological or chemical substance, such as hormones, a growth hormone, blood, enzymes, body fluids, body parts, body organs, body tissue, sperms, or eggs. The substance may comprise analyte indicators, analyte sensors and/or analyte detectors comprising any type of material. The analyte indicator or sensor may comprise, for example, a blood glucose test strip configured for indicating the blood glucose level or any other analyte monitoring strip configured to detect the presence of analyte. The blood glucose strip or analyte strip may comprise enzymes or any other biological or chemical materials. In another example, the analyte indicator or sensor may comprise urine test strips. The analyte indicator or sensor may comprise any diagnostic tool based on a biological indicator comprising a biological and/or chemical material. The substance may comprise cosmetics, such as lipsticks, perfumes, toiletries, hair or skin care products, sprays, mousses, emulsions and gels, for example. The substance may comprise, resins, adhesives, glues, epoxy or cyanoacrylate glue. The substance may be configured in any suitable form, such as a solid, liquid, emulsion, gas, gel, granules, or powder, for example. The substance may include more than one substance at the same or different phase, such as, for example, a liquid mixed with another liquid or a liquid mixed with a powder. Wherein the substance comprises a drug, the drug may include any suitable form such as a solid, powder, tablet, pill, capsule, gas, gel, cream, emulsion, spray, a suppository or a combination thereof and may be delivered in any suitable manner.

In some embodiments, the substance may be contained within a container 104.

In some embodiments, the container 104 may comprise a substance storage container or a substance delivery device or container. The container 104 may be configured in any suitable configuration for containing a substance therein. In some examples the container 104 may comprise a device for drug injection delivery such as an injection pen, a jet injector and/or a syringe. Some further non-limiting exemplary containers 104 for containing substances may include a substance vial, a substance cartridge, an ampoule, a substance pump, a pill box, a capsule container, an inhalator, a substance spraying device, an infusion device with a pump or an infusion device without a pump. In some embodiments, the container 104 may comprise a box. In some embodiments, the container 104 may comprise a container for storing and transferring blood glucose strips or any other analyte, e.g. a biologic or chemical analyte monitoring strips.

In some embodiments, the container 104 may comprise or may be comprised in an environmental control device and system as described in applicant's patent publication or as WO2016/011207 described in applicant's patent publications WO2017/090019, WO2020/084543 all publications incorporated herein in their entireties.

The container 104 is configured with an outer surface, including a proximal portion 105, a distal portion and a peripheral wall 106 extending in between. The container 104 may be arranged at least partially within a receiving volume 108 (also referred to as a "chamber") of the substance storage apparatus 100, as shown in FIG. 1C.

The substance storage apparatus 100 may comprise a housing 110 formed of a base 114 (1B) (e.g. a base portion) at a distal end 116 of the storage apparatus 100 and a lateral wall 120 extending longitudinally along a longitudinal axis x1 to a top portion 124 at a proximal end 126 of the storage apparatus 100. In some embodiments, the top portion 124 may be disposed within the storage apparatus 100, wherein a portion 130 of the housing wall partially overlies the top portion 124, as seen in FIG. 1B. In some embodiments the top portion 124 is not overlayed by the housing wall portion 130.

Figure 2B:
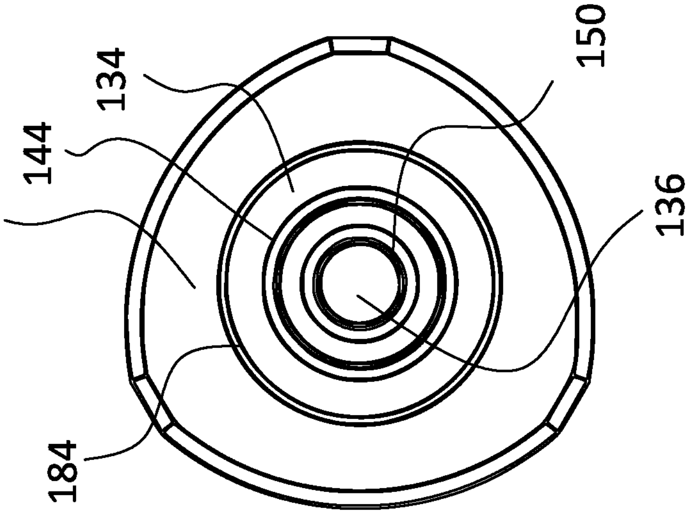
FIGS. 2A and 2B are schematic illustrations of an exemplary substance storage apparatus (2A) and a top view thereof (2B), constructed and operative according to some embodiments of the present disclosure.
Figure 2A:
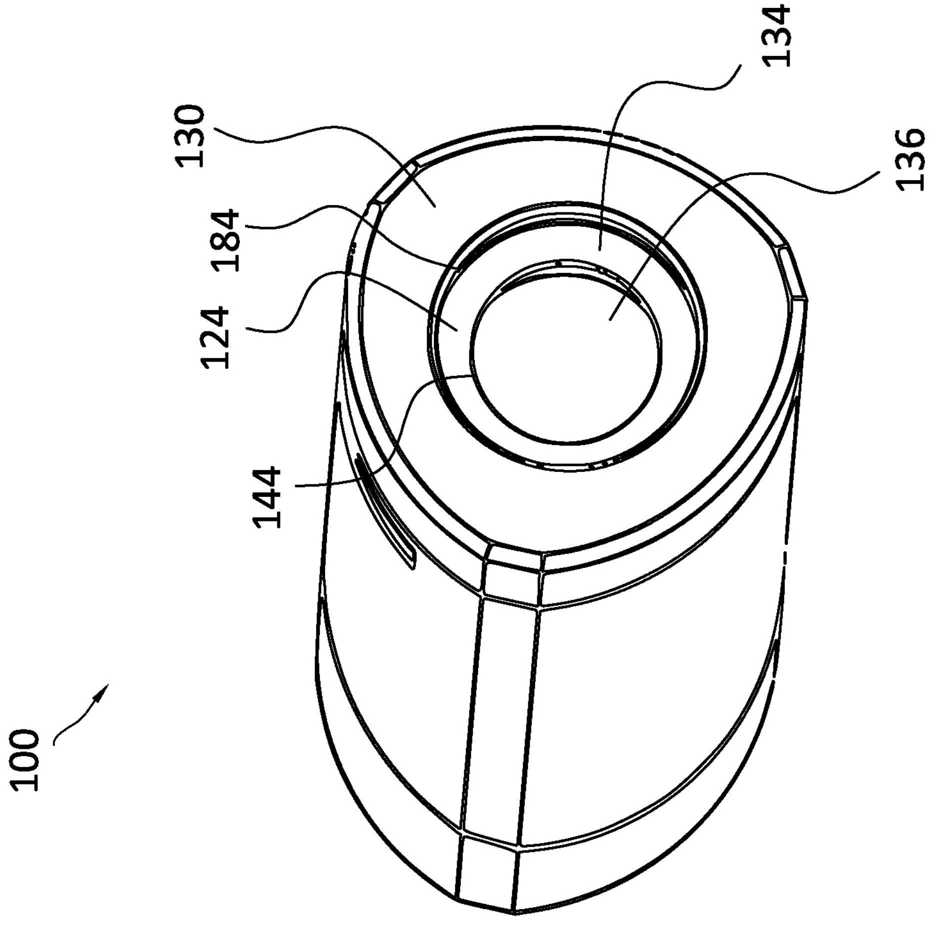

As seen in FIGS. 2A and 2B, in some embodiments, the top portion 124 comprises a cover 134 and an aperture 136 circumscribed at least partially by the cover 134 and configured for insertion of the substance-container 104 therethrough.

The wall 106 of the substance container 104 is formed of a first material, typically a rigid material. Different types of substance-containers may be dimensioned with a peripheral wall 106 of a different diameter. The cover 134 is formed, at least at a portion thereof, of a second material with a greater degree of resilience than the first material, thereby accommodating insertion therethrough of different types of substance-containers, where each substance-container is dimensioned with a peripheral wall 106 of a different diameter. The resilient material of cover 134 is operable to adapt to the wall 106 dimension (e.g. diameter) and shape. Accordingly, at least a portion of the resilient cover 134 grips the outer portion of the substance-container 104 with a sufficient degree of fiction so as to secure the substance container 104 within the receiving volume 108 of the housing 110.

Figure 3B:
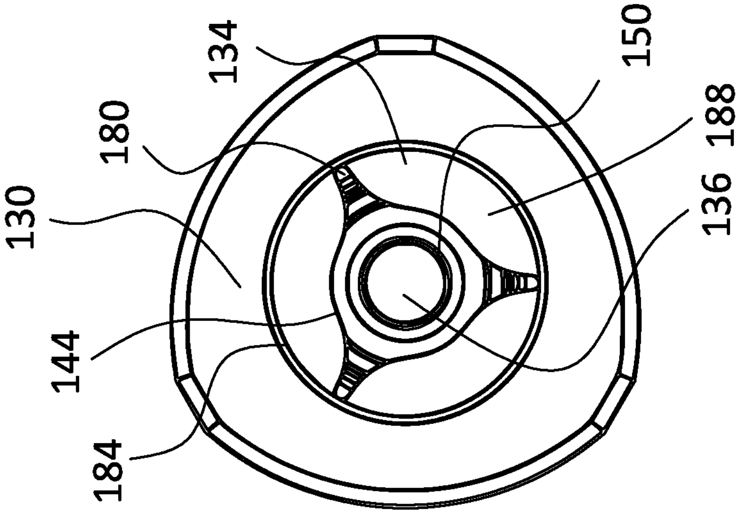
FIGS. 3A-D are schematic illustrations of an exemplary substance storage apparatus (3A), a top view thereof (3B), a substance storage apparatus with a substance-container inserted therein (3C) and a substance storage apparatus with another substance-container inserted therein (3D), constructed and operative according to some embodiments of the present disclosure.
Figure 3A:
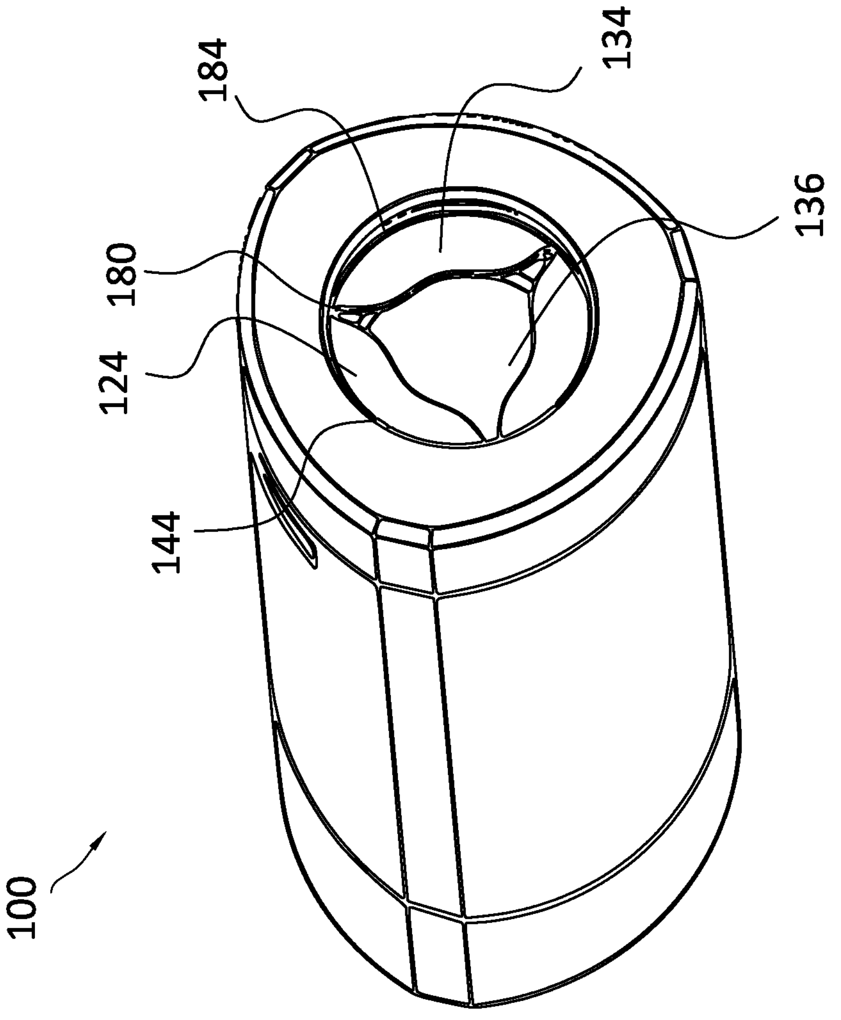
Figure 3D:
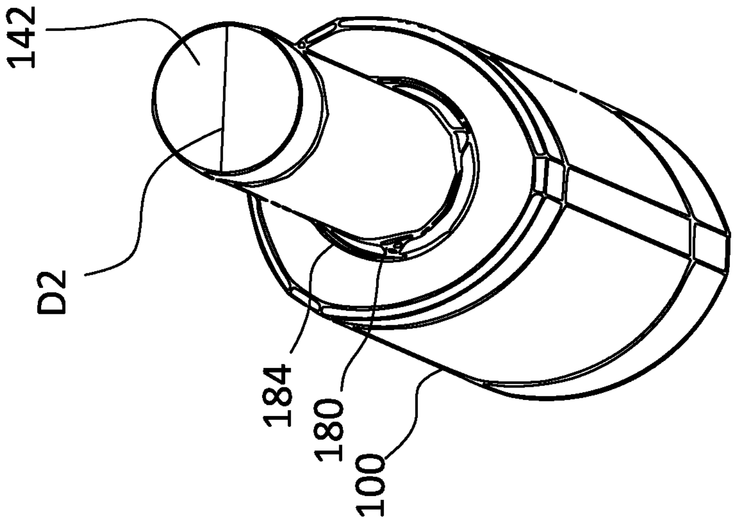
Figure 3C:
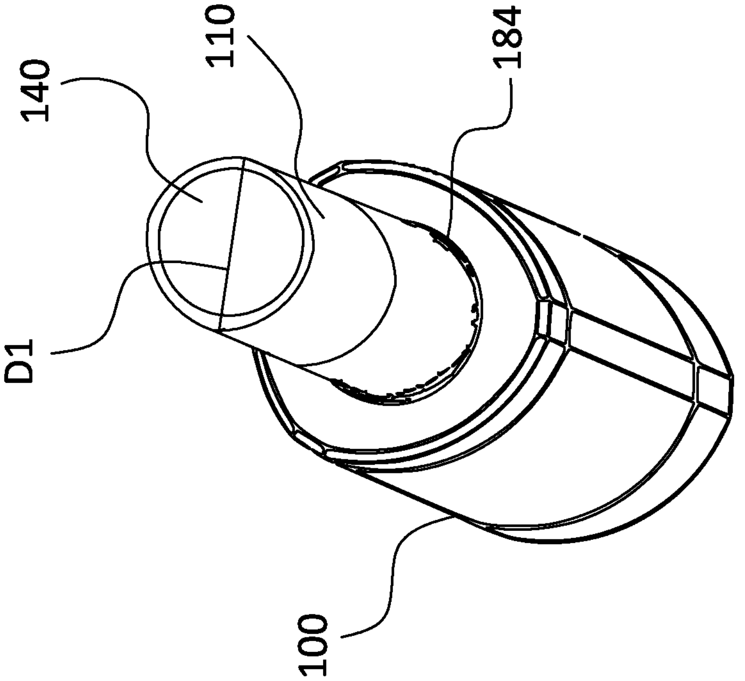
Figure 4B:
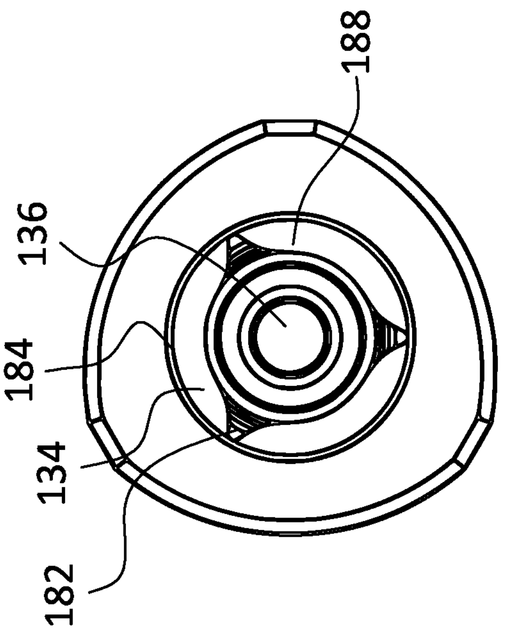
FIGS. 4A and 4B are schematic illustrations of an exemplary substance storage apparatus (4A) and a top view thereof (4B), constructed and operative according to some embodiments of the present disclosure.
Figure 4A:
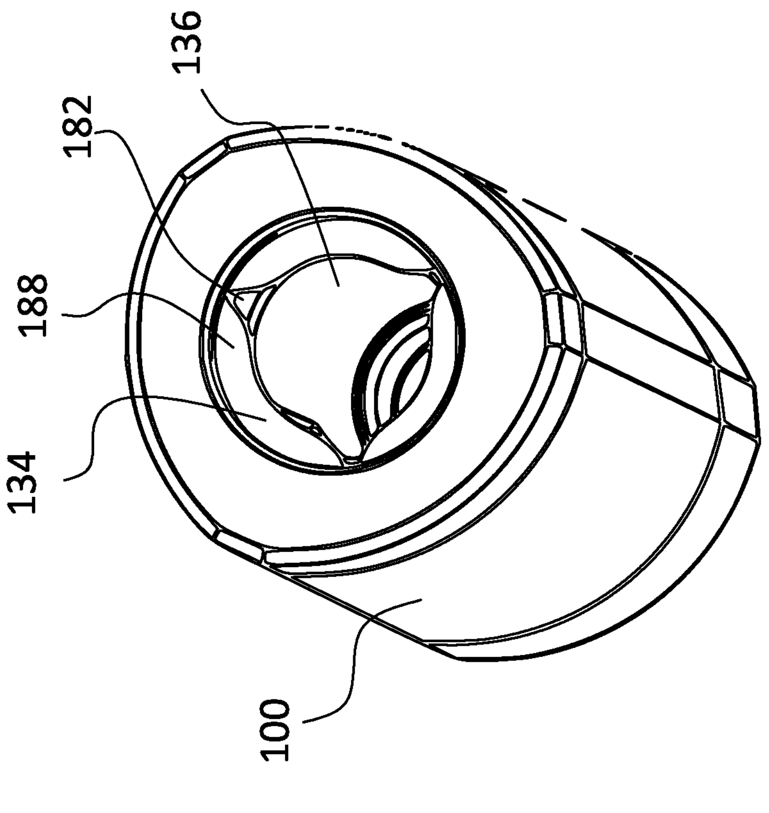

As seen in FIGS. 3C and 3D, a first substance-container 140 is sized with a larger diameter D1. (3C) than a second substance-container 142, sized with a smaller diameter D2 (3D). The resilient cover 134 adapts to the first and second substance-containers HO, 142 respectively, grips the first and second substance-containers 140, 142 and secures it in the receiving volume 108 of the housing 110.

In some embodiments, aperture 136 is sized with a diameter dimensioned to be equal or smaller than the wall diameter of the smallest substance container. In a hypothetical example, second substance-container 142 is sized with the smallest desired diameter. Aperture 136 may be sized with a diameter equal or smaller than the smallest diameter D2.

In some embodiments, providing the storage apparatus 100 with the resilient cover 134 facilitates omitting auxiliary adapters, which would have been otherwise required to accommodate the different sized substance containers 104 to the storage apparatus 100. Furthermore, providing the storage apparatus 100 with the resilient cover 134 facilitates deployment of a single top portion for different size substance-containers 104, without being required to switch top portions for each of the differently sized substance-container and without being required to add adaptors, where each adaptor designed to only fit a substance container of a predetermined diameter.

The resilient material may be defined as a material capable of being elastically deformed and which substantially rebounds to its original shape after deformation. Therefore, at least a portion of the resilient cover 134 is operable to expand or contract to the diameter of the inserted substance-container 104 while gripping and securing the substance-container 104 in the receiving volume 108 of the housing 110.

In a non-limiting example, the resilient material may comprise an elastomer, such as a thermoplastic elastomer. In a non-limiting example, the resilient material may comprise an elastic modulus in the range of 3-120 MPa, subranges and variants thereof. In a non-limiting example, the resilient material may comprise a tensile strength in the range of 100-4500 MPa at break, subranges and variants thereof.

In a non-limiting example, the resilient material may comprise an elongation at break ranging from 20 to 1350%, subranges and variants thereof.

In some embodiments, the resilient cover 134 may be circularly shaped with a substantially smooth inner circumference 144 surrounding the aperture 136 As seen in FIGS. 2A and 2B. In some embodiments, the resilient cover 134 may be shaped in any suitable configuration for accommodating differently sized substance containers 104. Further exemplary, non-limiting configurations of the cover 134 will be described in reference to FIGS. 3A-5B.

In some embodiments, the substance-container 104 is entirely enclosed within the volume 108 of the storage apparatus 100. In some embodiments, the storage apparatus 100 is configured for partial insertion of the substance-container 104 in the volume 108 and for partial protrusion of the substance-container 104 out of the top portion 124, as shown in FIGS. 1B and 1C.

In some embodiments, the substance-container 104 may be inserted within a receptacle 150 configured in any suitable shape for receiving the substance-container therein and disposed within the volume 108.

In some embodiments, the receptacle 150 may be formed with a peripheral wall 152 (1C) comprising any possible shape and defining therein a lumen configured with a predetermined diameter dimensioned to receive a reservoir region 154 of the substance-container 104 and being configured for containing the substance therein. In some embodiments, the aperture 136 of the top portion 124 may be configured with a diameter identical to or smaller than the predetermined lumen diameter. In some embodiments, the receptacle lumen is sized with a diameter dimensioned to be equal or larger than the wall diameter of the largest substance container. In a hypothetical example, first substance-container 140 is sized with the largest desired diameter D1, The receptacle lumen may be sized with a diameter equal or larger than the largest diameter D1.

In some embodiments, the receptacle 150 is shaped complementary to the shape of the substance-container 104. In the non-limiting example shown in FIGS. 1B and 1C, the substance-container 104 comprises an injection pen 156 (namely a substance-injection device) formed with a needle-containing region 158 which has a diameter smaller than a diameter of the reservoir region 154. The receptacle 150 is substantially similarly shaped with a corresponding reservoir region-receiving portion 160 dimensioned to receive the reservoir region 154 and a needle-containing region-receiving portion 162 configured and dimensioned to receive the needle-containing region 158. Further shapes and features of the receptacle 150 are described hereinbelow, such as in reference to FIGS. 6A-14.

Figure 1B:
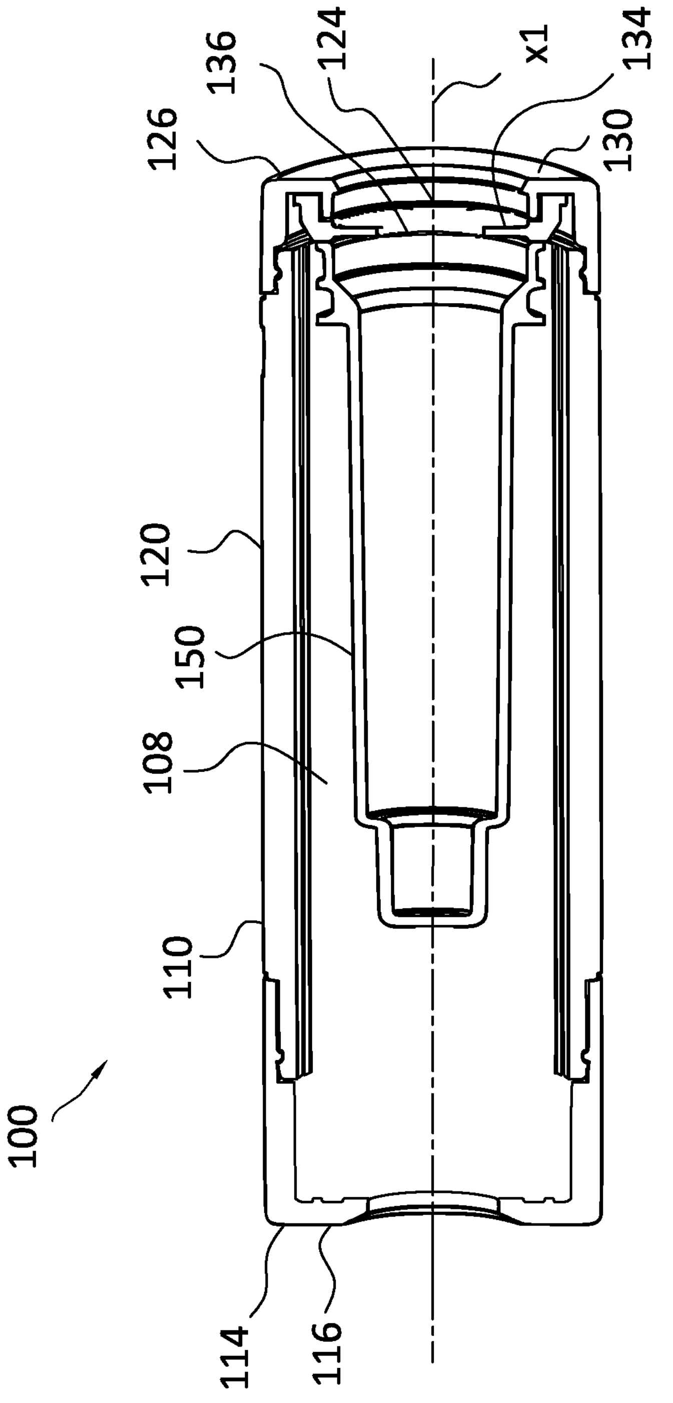
Figure 1C:
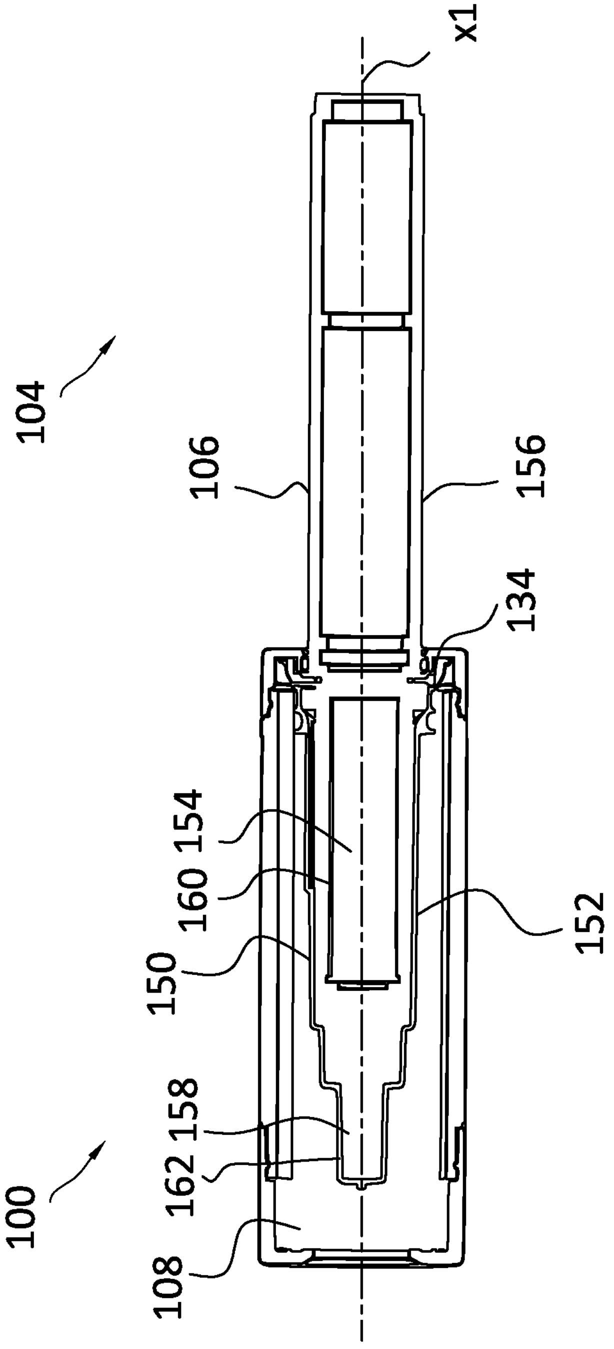
Figure 1D:
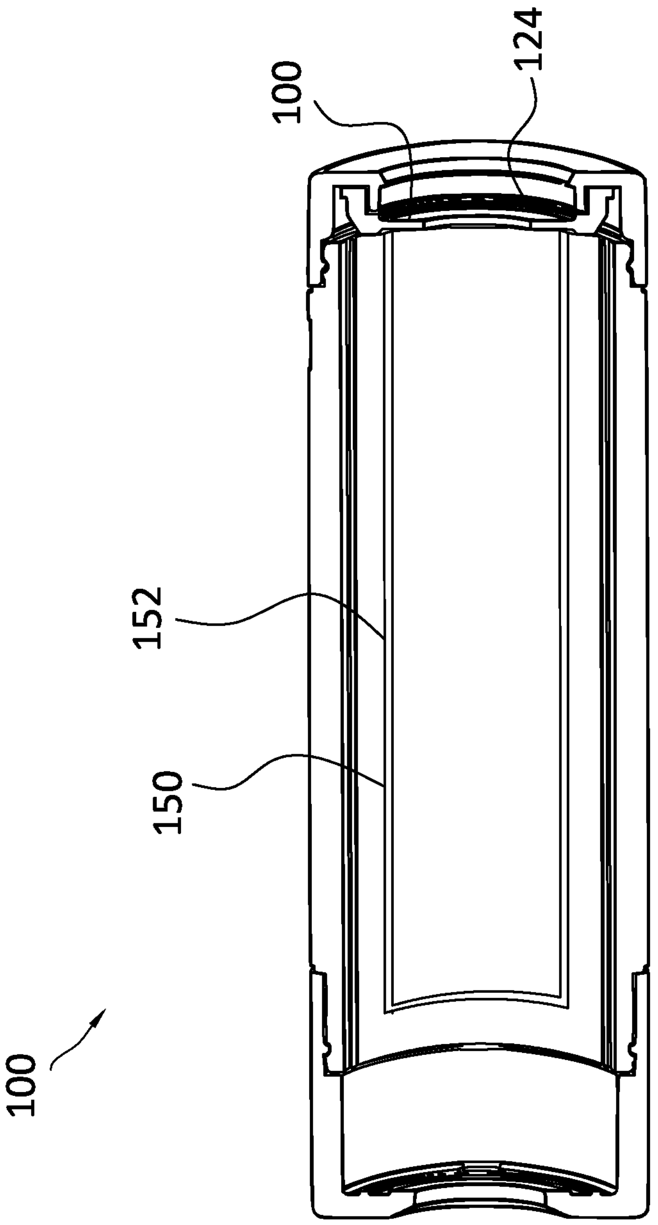

In some embodiments, the receptacle 150 may be cylindrically shaped, comprising a substantially linear peripheral wall 152, as shown in FIG. 1D. The cylindrically shaped receptacle 150 can receive substance-containers 104, such as injection pens, syringes, vials, pill boxes or any other type of substance-container 104 described hereinabove.

In some embodiments, the receptacle 150 may be omitted and the substance-container 104 may be inserted into the volume 108 of the storage apparatus 100.

In some embodiments, the volume 108 may be substantially empty, comprising mainly air.

Figure 1E:
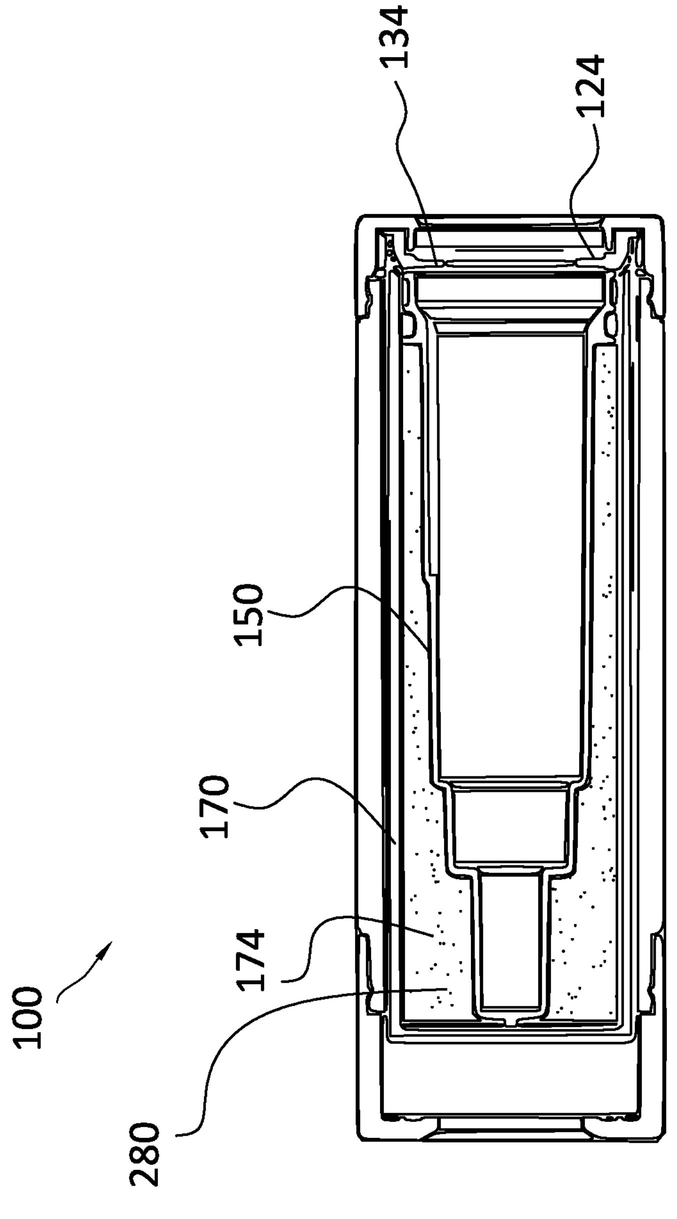

In some embodiments, the volume 108 may comprise environmental control elements provided to regulate the environmental conditions of the substance. Exemplary environmental control elements may include any one or more of thermal insulation element 170 and an energy absorbing material 174, such as a phase change material (PCM) element. In some embodiments, the substance-container 104 may be inserted directly within a volume containing the PCM element 174 and/or a volume containing the thermal insulation. In some embodiments, as shown in FIG. 1E, the receptacle 150 may be inserted within a volume comprising the PCM element 174 which may be surrounded by the thermal insulation 170.

In some embodiments, the thermal insulation element 170 may be disposed within the housing 110 being configured to provide a thermal shield to the substance. In some embodiments, the PCM element 174 is configured to thermally regulate the temperature of the substance and wherein the PCM element 174 is disposed within a PCM volume 280 formed intermediate at least a section of the receptacle 150 and at least a section of the thermal insulation element 170.

The storage apparatus 100 comprising the resilient cover 134 may or may not comprise some or more of the further features described in reference to FIGS. 6A-14.

Turning to FIGS. 3A-5B, it is shown that the top portion 124 may comprises at least one recess 180 extending from the aperture 136 and may terminate at an outer circumference 184 of the cover 134 or intermediate the inner circumference 144 and the outer circumference 184. In some embodiments two or more recesses 180 extend from the aperture 136. In some embodiments, the aperture 136 is centrally positioned at the top portion 124 and two or more equidistant recesses 180 extend from the aperture 136. FIGS. 3A-5B illustrate three equidistant recesses 180, yet it is appreciated that any number of recesses 180 may be provided at any distance therebetween.

Figure 5C:
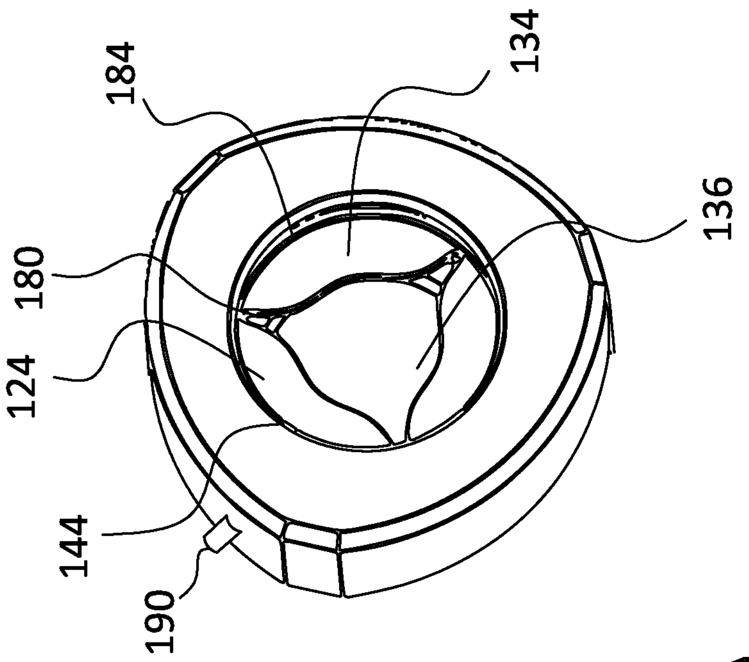
FIG. 5C is a schematic illustration of an exemplary top portion, constructed and operative according to some embodiments of the present disclosure.
Figure 5A:
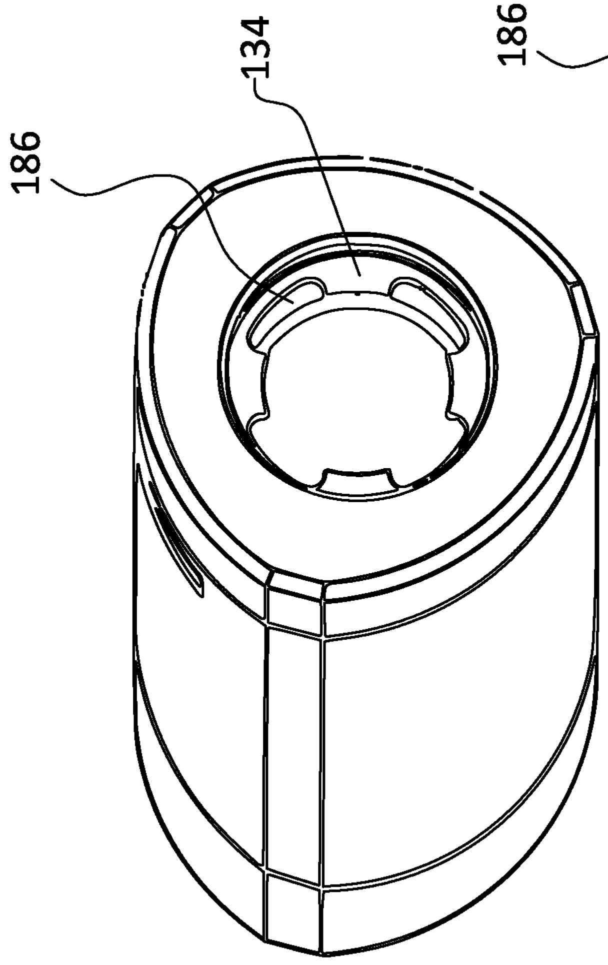
FIGS. 5A and 5B are schematic illustrations of an exemplary substance storage apparatus (5A) and a top view thereof (5B), constructed and operative according to some embodiments of the present disclosure.
Figure 5B:
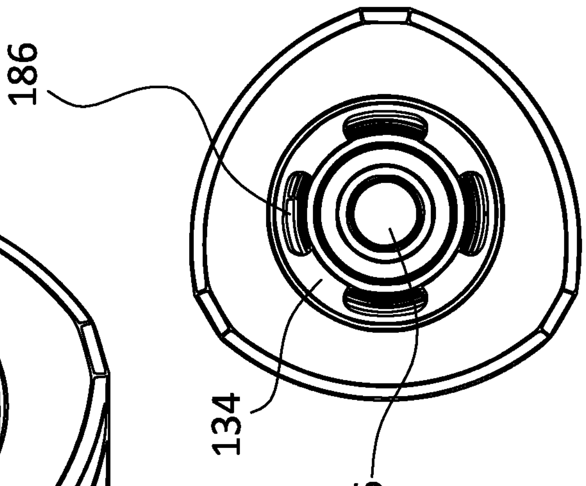

The recesses 180 may be formed in any suitable shape such as slits 182, as in the non-limiting example shown in FIGS. 3A-4B, or as orifices 186 configured in any suitable shape such an ovately shaped orifice as in the non-limiting example shown in FIGS. 5A and 5B, or the recesses may be formed in any other suitable shape and any type of opening.

The cover 134 may be formed of one or more flaps 188 or leaflets arranged in any suitable manner. In the non-limiting example shown in FIGS. 3A-4B, the flaps or leaflets are arranged so as to form a tricuspid valve-like shape.

As described hereinabove, the top portion 124 is configured to accommodate containers 104 of different diameters. As a wider container 140 (FIG. 3C) is inserted in the apparatus 100, the cover 134 (and in this configuration the recesses 180 as well), extend to a greater degree than when a narrower container 142 (FIG. 3D) is inserted in the apparatus 100. Thereby the top surface 124 is configured to accommodate containers 104 of different diameters (namely thicknesses, wider or narrower).

Turning to FIG. 5C it is shown that in some embodiments, the top portion 124 may be formed with universal attachment means 190, such as snaps, an adhesive or any other suitable means configured for attaching the top surface 124 to any type, and shape of a substance storage apparatus. Accordingly, top portion 124 can be provided separately from the housing 110 and is configured to fit many types of substance storage apparatuses.

FIGS. 6A-9 illustrate features of a substance storage apparatus 200 comprising an environmental control element provided to regulate the environmental conditions of the substance. It is noted that in some embodiments, all or part of these features can be included in the apparatus 100 which comprises the top portion 124 or in any other substance storage apparatus described herein. In some embodiments, the apparatus 200 is formed with a rigid top portion 124.

In some embodiments, the thermal insulation element 170 may comprise an evacuated chamber, such as a vacuum formed intermediate two walls formed by the thermal insulator closure. In some embodiments, the thermal insulator closure may comprise a vacuum insulated panel (VIP) comprising a gas-tight enclosure surrounding a rigid core, from which the air has been evacuated. In some embodiments, the thermal insulator closure may comprise a multi-layered material formed of walls and evacuated gap, which may be commercially available as INSULON®, made by Concept Group, Inc. (www.conceptgroupinc.com), as well as similar constructions disclosed in U.S. Publication No. 20140090737, incorporated herein by reference in its entirety. In some embodiments, the thermal insulator closure may comprise a relatively high-vacuum structure. In a non-limiting example, the high-vacuum may be about $10^{-3}$ torror less, or about $10^{-4}$ torr or less, or may be about $10^{-5}$ torr or less, or may be about $10^{-6}$ torr or less, or may be about $10^{-7}$ torror less.

Figure 6A:
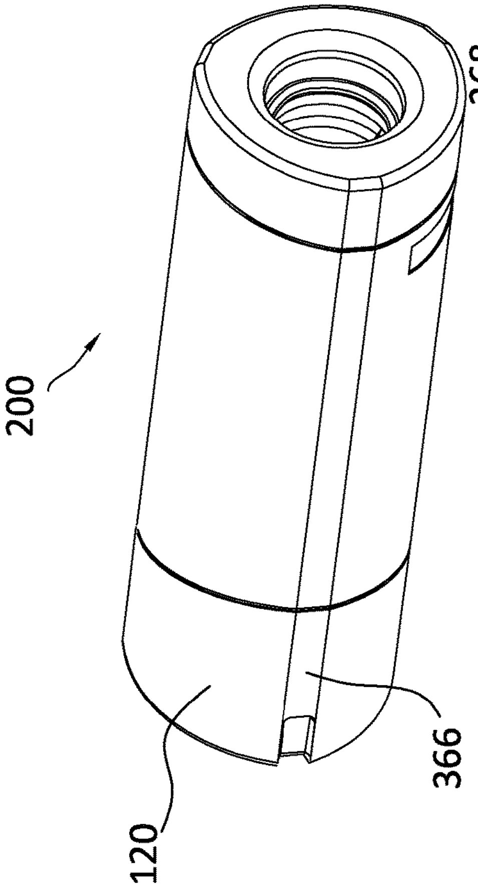
FIGS. 6A and 6B are schematic illustrations of an exemplary substance storage apparatus (6A) and a sectional view of the of FIG. 6A (6B), constructed and operative according to some embodiments of the present disclosure.
Figure 6B:
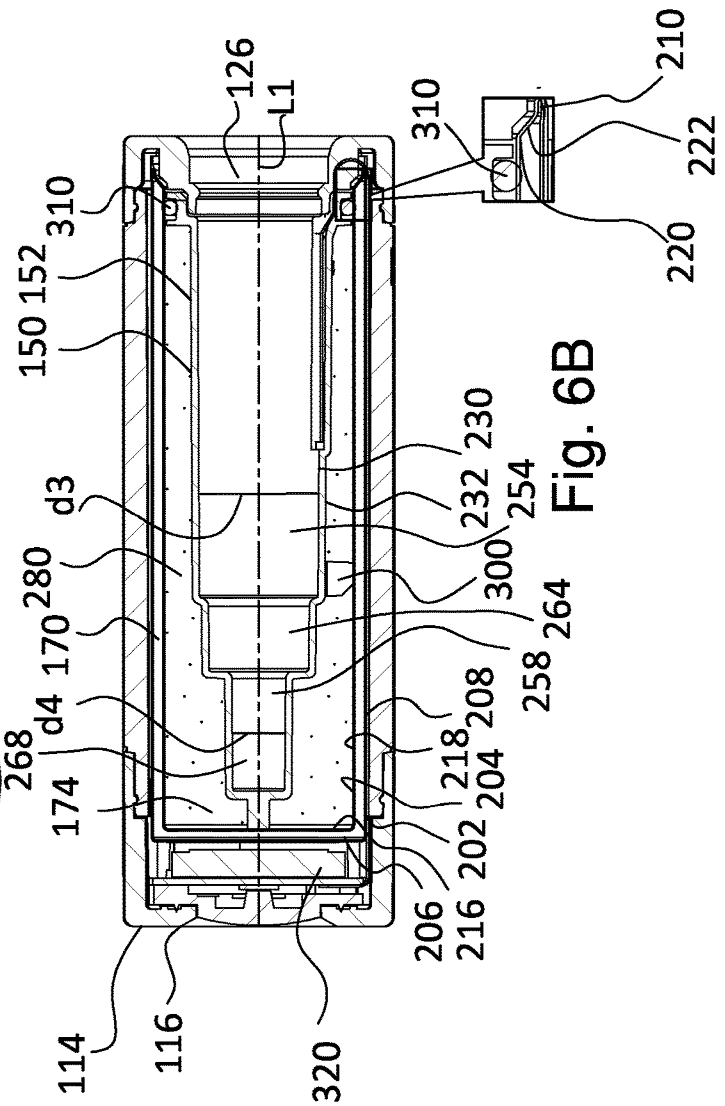
Figure 7A:
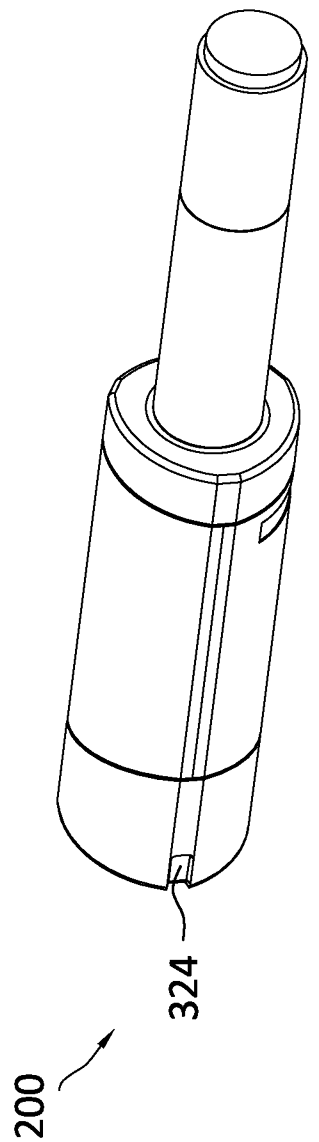
FIGS. 7A and 7B are schematic illustrations of the substance storage apparatus of FIG. 6A with a substance-container inserted therein (7A) and a sectional view of the of FIG. 7A (7B), constructed and operative according to some embodiments of the present disclosure.
Figure 7B:
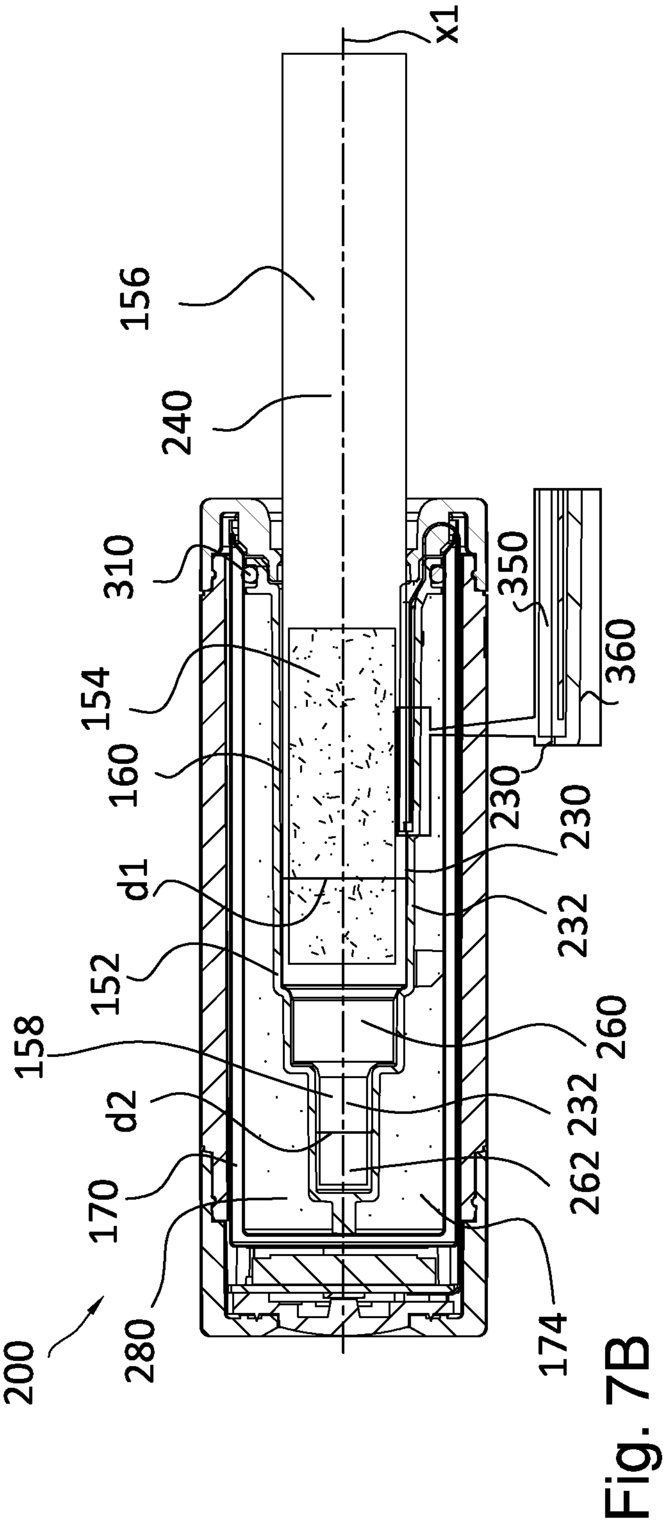
Figure 9:
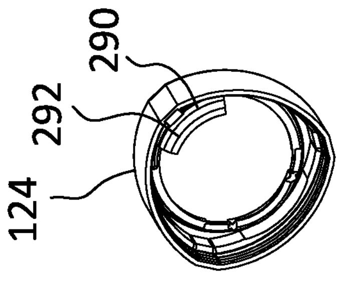
FIG. 9 is a schematic illustration of atop portion of a substance storage apparatus, shown at an underside thereof, constructed and operative according to some embodiments of the present disclosure.

In some embodiments, as shown in FIG. 6B, the thermal insulation element 170 may comprise an external cylinder 202 and an internal cylinder 204. The external cylinder 202 is formed with an external base portion 206 and an external peripheral wall 208 extending longitudinally from the external base portion 206 to a first lip 210 thereof. The internal cylinder 204 is formed with an internal base portion 216 and an internal peripheral wall 218 (namely an inner wall 218) extending longitudinally from the internal base portion 216 to a second lip 220. A rim 222 connects the first lip 210 to the second lip 220. The external cylinder 202, the internal cylinder 204 and rim 222 are configured to enclose the thermal insulation element and define an enclosed chamber intermediate the external cylinder 202 and the internal cylinder 204 In some embodiments, the enclosed chamber may be evacuated forming the evacuated chamber.

In some embodiments, the enclosed chamber may comprise other materials, such as air, other gases, liquids or solids.

In some embodiments, the thermal insulation element 170 may comprise silicon, aerogel, air or any other gas or other materials, such for a non-limiting example, fiberglass, wool, cellulose, foams and/or polystyrene.

In some embodiments, the walls 208 and 218 may be formed of any suitable material the which can be rigid or flexible. In some embodiments, the thermal insulation element 170 is enclosed at its distal end 116 by a base portion (e.g. comprising the external base portion 206 and/or the internal base portion 216) or any other configuration of a base portion, and is configured with an opening at the proximal end 126.

In some embodiments the external cylinder 202 and the internal cylinder 204 and rim 222 may be formed of a thermally conducting material such as stainless steel and the thermal insulation is provided by the evacuated chamber formed in between.

In some embodiments the external cylinder 202 and the internal cylinder 204 and rim 222 may be formed of a thermal insulating material or of a combination of thermal conducting materials and thermal insulating materials.

In some embodiments, several thermal insulation elements and/or materials having the same or different insulating properties may be used to achieve specific characteristics (e.g. degree of thermal insulation, predetermined temperature in the substance for controlling and/or maintaining the environmental conditions of the substance).

It is noted that the configurations of the thermal insulation element 170 described hereinabove may be implemented in any one of the apparatuses (e.g. 100, 200, 400, 550 and cap assembly 550) described in reference to FIGS. 1A-14.

In some embodiments, the peripheral wall 152 of the receptacle 150 may comprise an internal surface 230 and an external surface 232. The receptacle 150 may be configured with a shape complementary to a shape of the substance-container 104 for securely receiving the substance-container 104 with minimal or no gaps between the internal surface 230 and the peripheral wall 106 of the substance container 104. This is shown in the non-limiting example of FIGS. 6A-8 where the substance-container 104 comprises the injection pen 156 (7B) configured with the substance reservoir region 154 disposed along the longitudinal axis thereof (which may converge with longitudinal axis x1 when inserted in the receptacle 150), intermediate a plunger region 240 positioned at a first end thereof, and the needle-containing region 158 positioned at a second end thereof. It is noted that the scale and length of the reservoir region 154, plunger region 240 and needle-containing region 158 may vary between injection pens 156 and may be not shown to scale.

The receptacle 150 may be configured with a length L1 (FIG. 6B) along its longitudinal axis x1 dimensioned to receive the needle-containing region 158 and the reservoir region 154, such that at least a portion of the plunger region 240 protrudes from the top portion 124 of the apparatus 200.

In some embodiments, the injection pen 156 (FIG. 7B) comprises a first container portion substantially perpendicular to the longitudinal axis x1 and disposed at the reservoir region 154. The first container portion is configured with a first diameter d1. Substantially parallel to the first container portion is a second container portion disposed at the needle-containing region 158, the second container portion is configured with a second diameter d2, which is smaller than the first diameter d1. The receptacle 150 may be shaped complementary to the shape of the injection pen 156 in which the receptacle 150 comprises a reservoir region-receiving portion (FIG. 6B) configured with a first receptacle-portion 254 (e.g. reservoir region-receiving portion 160) sized with a first diameter d3 and being dimensioned to receive the reservoir region 154.

The receptacle 150 comprises a needle-containing region-receiving portion 258 (e.g. needle-containing region-receiving portion 162) configured with a second receptacle portion including a second diameter d4 and being dimensioned to receive the needle-containing region 158, where the second diameter d4 of the second receptacle portion is smaller than the first diameter of the first receptacle portion d3. It is noted that the injection pen 156 may comprise further portions or sub-portion, such as the needle-containing region 158 which may comprise at least a first sub-portion 260 and a second sub-portion 262. The sub-portions may be formed with a successively smaller diameter. Accordingly, the receptacle 150 may be formed with a complementary shape, where its needle-containing region-receiving portion 258 is formed of a first and second sub-portion 264 and 268 (6B), respectively, and each sub-portion is formed with a successively smaller diameter In some embodiments, the receptacle 150 comprises the reservoir region-receiving portion 254 dimensioned to snugly receive the reservoir region 154. The needle-containing region-receiving portion 258 is dimensioned to snugly receive the needle-containing region 158.

In some embodiments, the PCM element 174 is disposed within a PCM volume 280 defined between the external surface 232 of the receptacle 150 and the inner wall 218 of the thermal insulation element 170.

In some embodiments, the PCM volume 280 contains the PCM element 174 with minimal or no air gaps therein. In some embodiments, the PCM element 174 is positioned to at least partially or fully surround the external surface 232 of the receptacle 150. In some embodiments, the PCM element 174 is positioned in partial or full contact (namely contiguous) with the external surface 232 of the receptacle 150 and/or is positioned in partial or full contact with the inner wall 218 of the thermal insulation element 170.

In some embodiments, the PCM element 174 is inserted into the PCM volume 280 in an at least partially liquid state. During assembly of the apparatus 200 the PCM element 174 is initially in an at least partially liquid state, such that it is poured into a volume defined by the inner wall 218 of the thermal insulation element 170 prior to insertion of the receptacle 150 in the apparatus 200. Thereafter, the receptacle 150 is inserted in the PCM element 174, such that the PCM element 174 fills the PCM volume 280.

In some embodiments, the housing 110 is formed with at least one retainer 290 (FIG. 9) for preventing the receptacle 150 from being axially displaced in response to expansion of the PCM element 174 within the PCM volume 280, such as when in an at least partial liquid state. The retainer 290 may be formed in any suitable configuration, such as a protrusion 292 extending from a top portion 124 or any other location of the apparatus 200.

Figure 8:
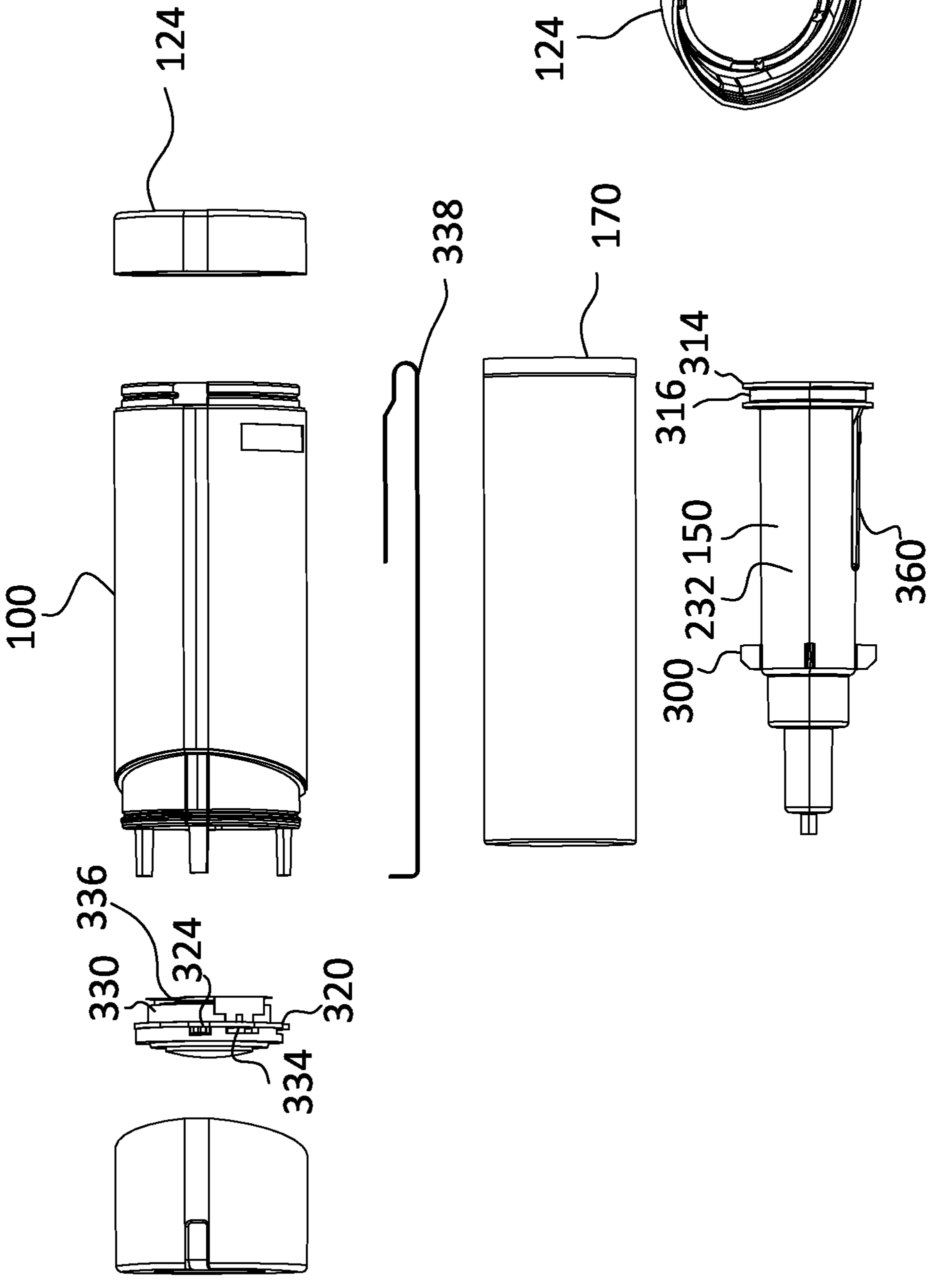
FIG. 8 is an exploded view of the substance storage apparatus of FIG. 6A, constructed and operative according to some embodiments of the present disclosure.

In some embodiments, the receptacle 150 comprises at least one lateral projection 300 protruding from the external wall 232 of the receptacle 150 and is configured for positioning the receptacle 150 within the PCM volume 280. In some embodiments, the lateral projection 300 comprises two, three or more lateral projections or as shown in FIG. 8.

In some embodiments, the projection 300 is formed of a material with a degree of thermal conductivity equal to or greater than the degree of thermal conductivity of the PCM element 174. In some embodiments, the degree of thermal conductivity may be slightly greater than the degree of thermal conductivity of the PCM element 174, such as even greater by a degree of 0.05 watts per meter-kelvin (W/m·K) or more; or greater by a degree of 0.1 (W/m·K) or more, in a non-limiting example.

To further seal the apparatus 200 a sealing element 310 (FIG. 7B) (e.g. a gasket, O-ring or any other suitable sealant) is disposed in proximity to the top portion 124. In some embodiments, the receptacle 150 comprises at least a pair of peripheral protrusions 314 defining a groove 316 therebetween configured for housing the sealing element 310, as seen in FIG. 8.

The apparatus 200 may comprise a power unit 320 for powering some components of the apparatus 200 such as an indicator 324 (e.g. a LED in a non-limiting example) and/or a sensor, as will be further described. The power unit 320 may comprise components such as a battery 330, a processor 334 and electronics 336 and any other related element, such as a switch or an activation button. Electrical communication between the power unit 320 and other components in the apparatus 200 may be facilitated in ay suitable manner such as via an electrical conductor 338 configured any suitable manner.

In some embodiments, the power unit 320 is disposed intermediate the base portion 114 of the housing 110 and the base portion (e.g. external base portion 206) of the thermal insulation element 170.

In some embodiments, the apparatus 200 comprises a temperature sensor 350 configured to measure the temperature of the substance when contained in the substance-container 104 within the substance reservoir region 154. The temperature sensor 350 may be disposed at any suitable location in the apparatus 200. In some embodiments, the temperature sensor 350 may be disposed in proximity to the substance reservoir region 154. For example, the temperature sensor 350 may be disposed at or in proximity to the reservoir region-receiving portion 160 of the receptacle 150. The receptacle 150 may be formed with a protuberance 360 protruding from an internal wall 230 of the receptacle 150 at the reservoir receiving-portion 160. The protuberance 360 is configured for housing the temperature sensor 350 and positioning the temperature sensor 350 facing the substance reservoir region 154. Positioning the temperature sensor 350 in proximity to the substance reservoir region 154 provides for enhancing the accuracy of the measured substance temperature.

In some embodiments, the lateral wall 120 of the housing 110 is formed with at least one flat surface 366 (FIG. 6A) configured to prevent rolling of the apparatus 200 on a substantially flat surface.

FIGS. 10-12B illustrate apparatuses 400 comprising a thermal conducting element. Apparatus 400 may comprise some or all features of the apparatuses 100 and 200.

As described herein, the thermal insulation element 170 may be formed of an evacuated chamber formed between the external peripheral wall 208 and the internal peripheral wall 218 or by any other insulation, typically extending along the lateral wall 120 of the housing 110. This configuration provides high thermal insulation to the reservoir region 154 of the container 104 as heat, illustrated by arrow 402 (positioned parallel to a central axis x2, which transverses the longitudinal axis x1) is prevented from penetrating the lateral wall 120. In some embodiments, heat can penetrate the apparatus 400 via an exposed region 410 defined at a location in the apparatus 400 which lacks the thermal insulation element 170, such as proximal to the proximal end 126. The heat can penetrate into the PCM volume 280 and generally flow parallel to the lateral wall 120 along arrows 430 from the proximal end 126 towards the distal end 116.

Since in some embodiments the material of the PCM element 174 may comprise poor thermal conductivity, less heat flows towards the distal end 116 causing a heat gradient parallel to longitudinal axis x1. With the central axis x2 serving as a reference line, there is a higher concentration of heat at a location closer to the proximal end 126 and a lesser concentration of heat at a location closer to the distal end 116. In a non-limiting example, the heat gradient may be 15° C. or lower. Accordingly, the PCM element 174 disposed in the PCM volume 280 located closer to proximal end 126, may be in a liquid state or in a partially liquid state, while the PCM element 174 disposed in PCM volume 280 located closer to distal end 116 may be in a solid state or in a partially solid state. This indicates that the PCM element 174 is not sufficiently absorbing the heat at the location closer to the distal end 116.

In some embodiments, the apparatus 400 may comprise a thermally conducting element 440 disposed within the PCM volume 280. The thermally conducting element 440 may be disposed within the PCM volume 280 at least at a location closer to the distal end 116 than the proximal end 126, so as to compensate for the lower thermal conductivity of the PCM element 174 disposed at the location closer to the distal end 116 and provide uniform distribution of heat within the PCM volume 280.

In some embodiments, the thermally conductive element 440 is not disposed within the PCM element 174 within the PCM volume 280 at a location closer to the proximal end 126 than the distal end 116.

The thermally conducting element 440 is configured with a thermal conductivity greater than the thermal conductivity of the PCM element 174. In some embodiments, the thermally conducting element 440 is configured with a thermal conductivity slightly greater than the thermal conductivity of the PCM element 174. In a non-limiting example, the thermally conducting element 440 is configured with a thermal conductivity greater than 0.05 W/(m*K) or more than the thermal conductivity of the PCM element 174. In a non-limiting example, the thermally conducting element 440 is configured with a thermal conductivity greater than 0.1 W/(m*K) or more than the thermal conductivity of the PCM element 174. In a non-limiting example, the PCM element 174 may have a thermal conductivity of 0.1-02 W/(m*K) and the thermally conducting element 440 is formed of a plastic material, such the lateral projection 300 (FIG. 6B), which has a thermal conductivity of 0.2-03 W/(m*K) or more.

In a non-limiting example, the thermally conducting element 440 is configured with a thermal conductivity greater than 10 W/(m*K) or more than the thermal conductivity of the PCM element 174. In a non-limiting example, the PCM element 174 may have a thermal conductivity of 0.1-02 W/(m*K) and the thermally conducting element 440 is formed of a metallic material having a thermal conductivity of 10.1 W/(m*K) or more.

In some embodiments, thermally conducting elements 440 may be formed of different materials with different levels of thermal conductivity.

The thermally conducting element 440 may be formed in any suitable configuration. The thermally conducting element 440 may comprises at least one thermally conducting protrusion 444 or a plurality of protrusions. The thermally conducting protrusion 444 may protrude from the external surface 232 of the receptacle 150 into the PCM volume 280. The thermally conducting protrusion 444 may comprise the lateral projection 300 (FIG. 6B) laterally protruding into the PCM volume 280.

In some embodiments, the plurality of protrusions 444 may be equidistantly arranged about the external surface 232.

Figure 10:
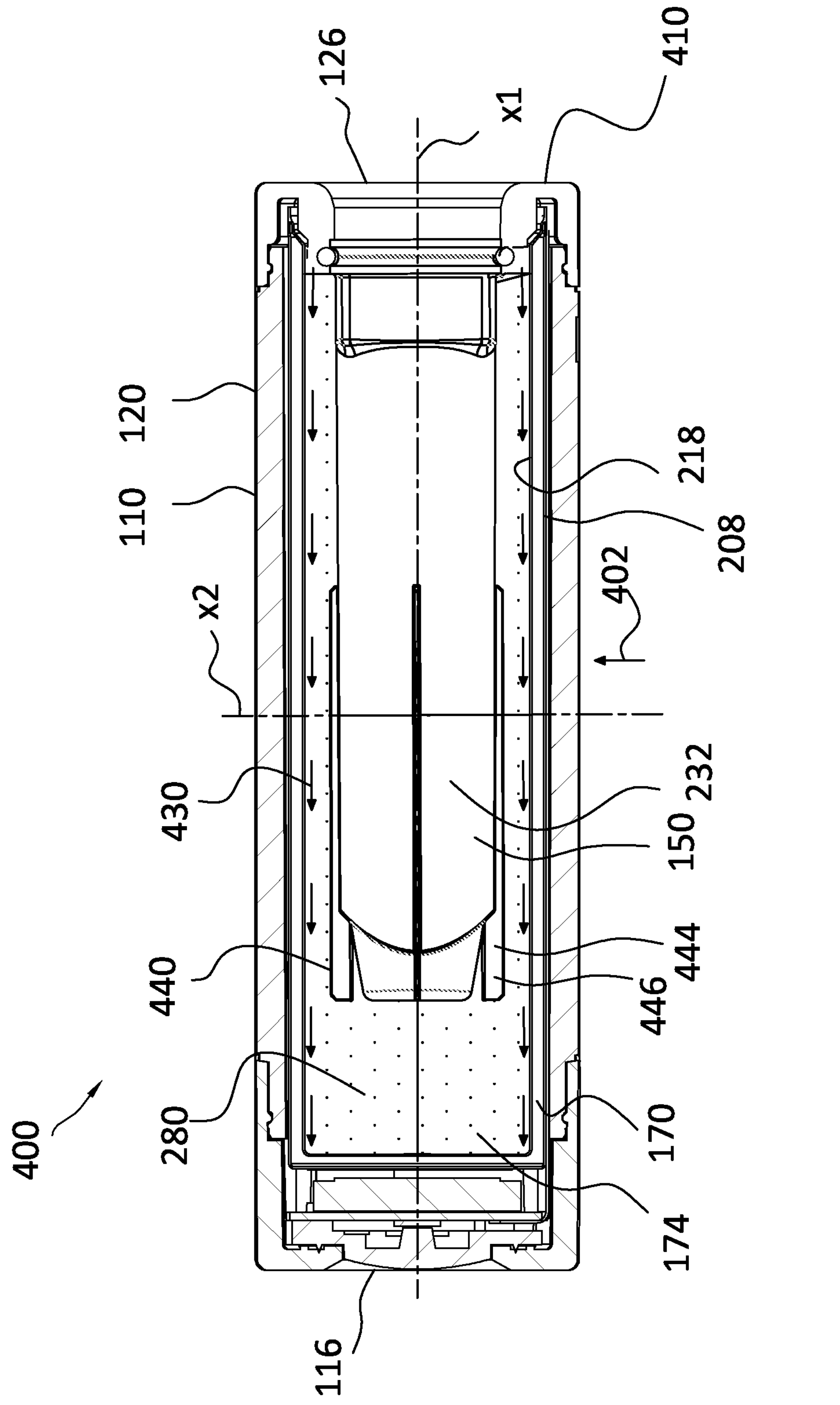
FIG. 10 is a schematic sectional illustration of an exemplary substance storage apparatus comprising a thermal conducting element, constructed and operative according to some embodiments of the present disclosure.
Figure 11A:
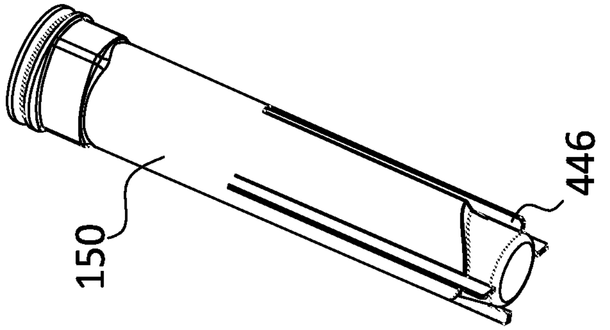
FIGS. 11A-C are each a schematic illustration of an exemplary receptacle comprising a thermal conducting element, each showing a different embodiment, constructed and operative according to some embodiments of the present disclosure.
Figure 11B:
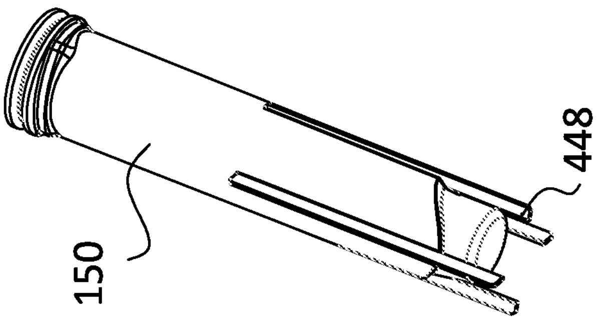
Figure 11C:
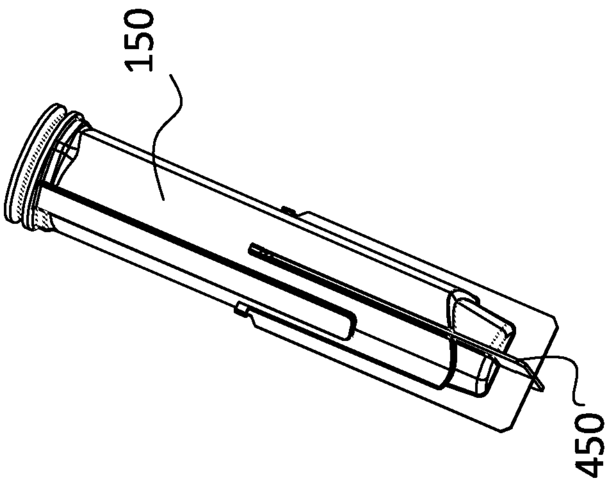

As seen in FIGS. 10-11C, the thermally conducting protrusion 444 may comprise an elongated body 446 extending longitudinally (i.e. axially) towards the distal end 116. FIGS. 10 and 11A show the thermally conducting protrusion 446 extending axially from the receptacle 150. FIG. 10 shows the receptacle 150 of FIG. 11A assembled in the apparatus 400.

FIGS. 11B and 11C show different alternative embodiments of the thermally conducting elements 400 extending from the receptacle 150. In FIG. 11B the thermally conducting protrusion 448 extends axially to a greater degree into the PCM volume 280 than the thermally conducting protrusion 446 of FIG. 11A. As seen in FIG. 11C, a plurality of protrusions 450 are arranged bisectionally at the distal end 116 of the receptacle 150.

In some embodiments, such as shown in FIGS. 10-11C, the thermally conducting protrusions 444 are arranged to protrude into the PCM volume 280 such that at least two surfaces of the thermally conducting protrusions 444 are incontiguous with the external surface 232 of the receptacle 150.

Figure 12A:
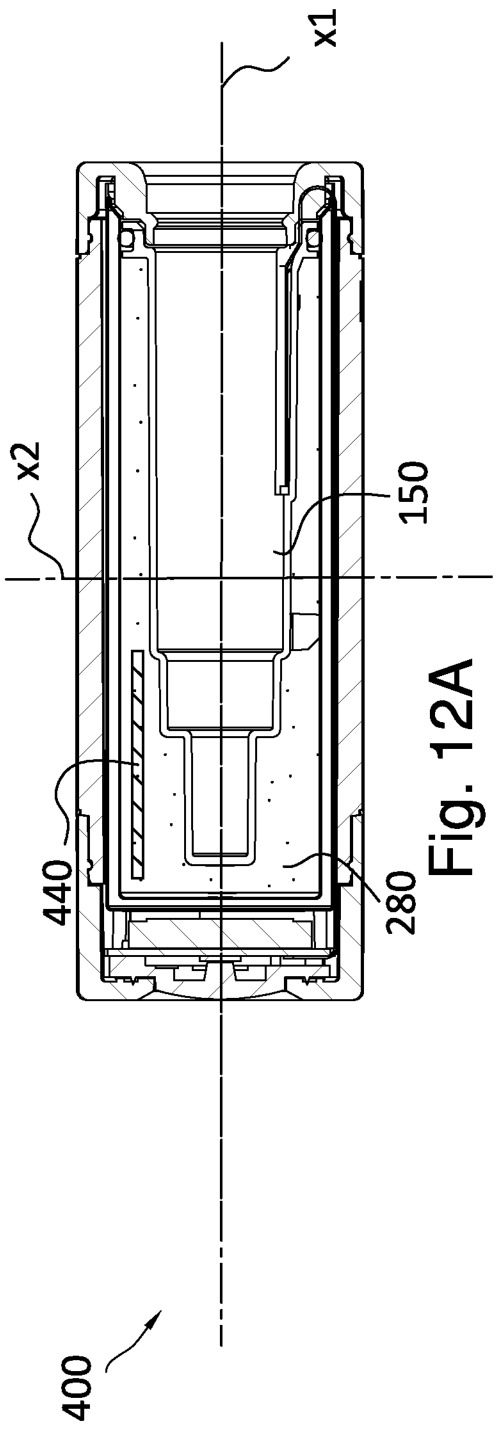
FIGS. 12A and 12B are each a schematic illustration of an exemplary substance storage apparatus comprising a thermal conducting element, each showing a different embodiment, constructed and operative according to some embodiments of the present disclosure.

In some embodiments, as shown in FIG. 12A, the thermally conducting element 440 may be entirely disposed within the PCM volume 280 and may be incontiguous with the receptacle 150.

Figure 12B:
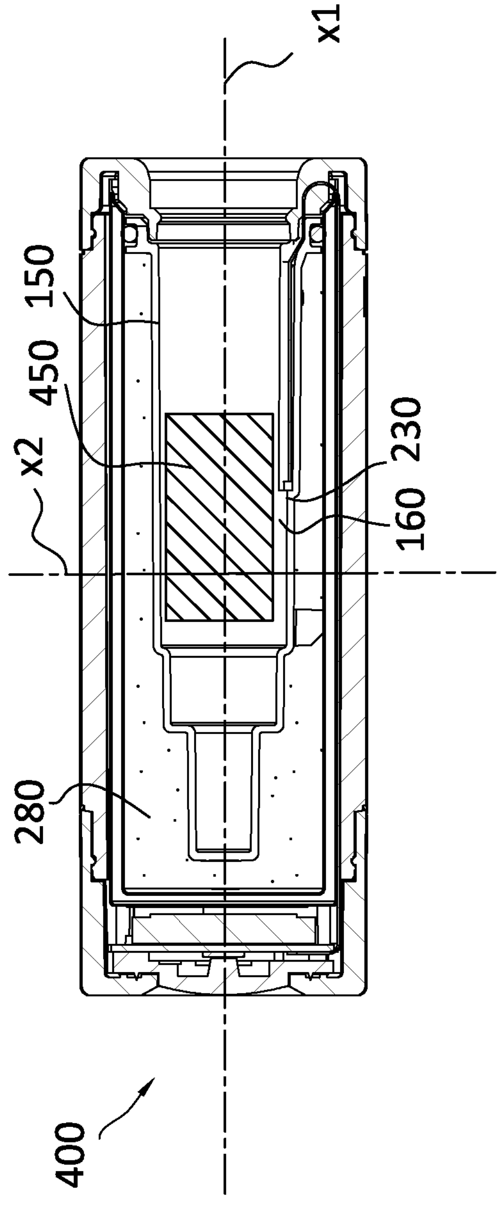

In some embodiments, as shown in FIG. 12B, the thermally conducting element 440 comprises a foil 450 or other layer at least partially circumscribing the internal surface 230 of the receptacle 150 and arranged to at least partially surround the reservoir region-receiving portion 160 so as to be proximal to the reservoir region 154 of the container 104.

Figure 13A:
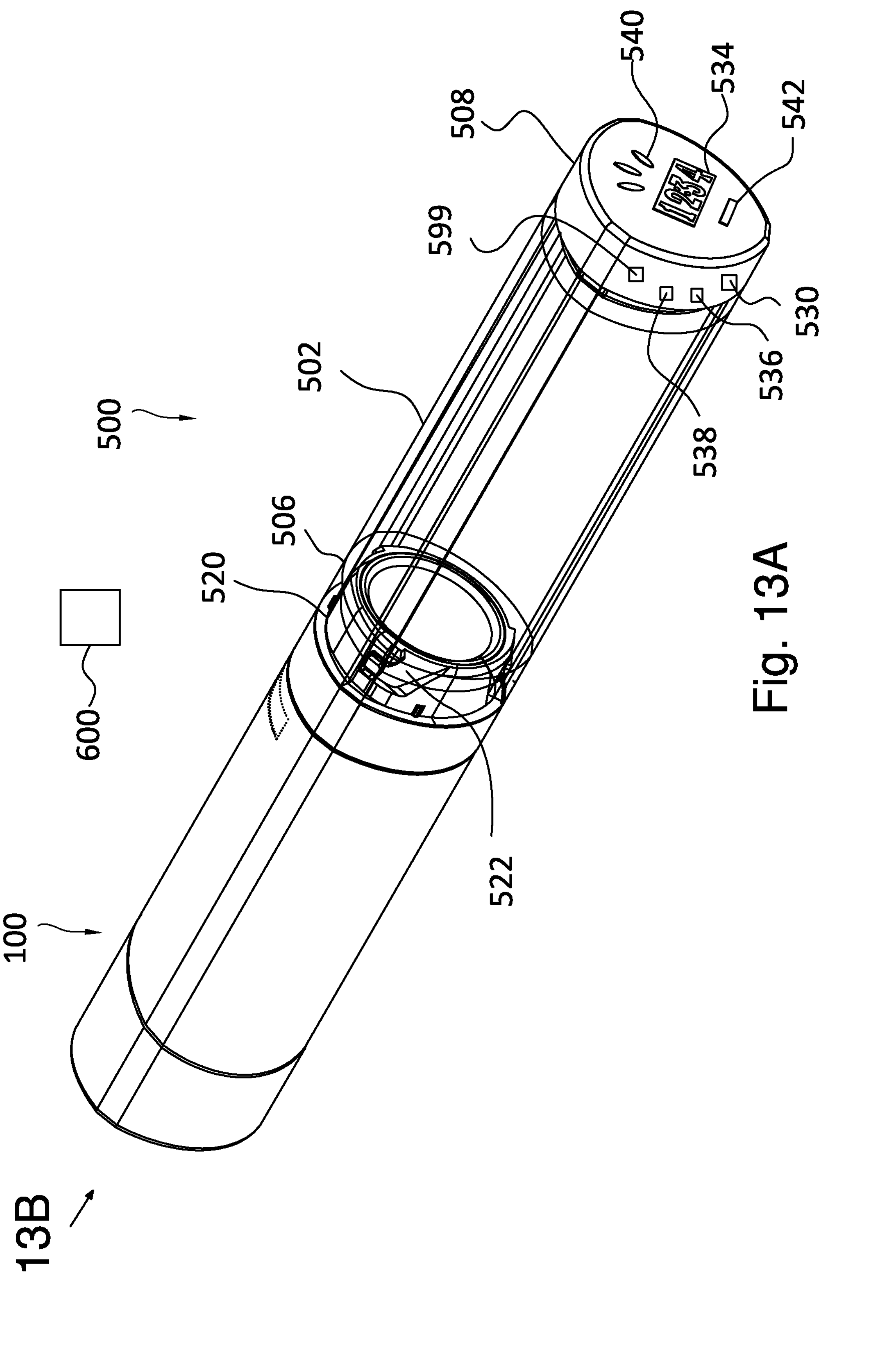
FIGS. 13A and 13B are schematic illustrations of an exemplary substance storage apparatus and a cap assembly shown at a first view (13A) and a second view (13B), constructed and operative according to some embodiments of the present disclosure.
Figure 13B:
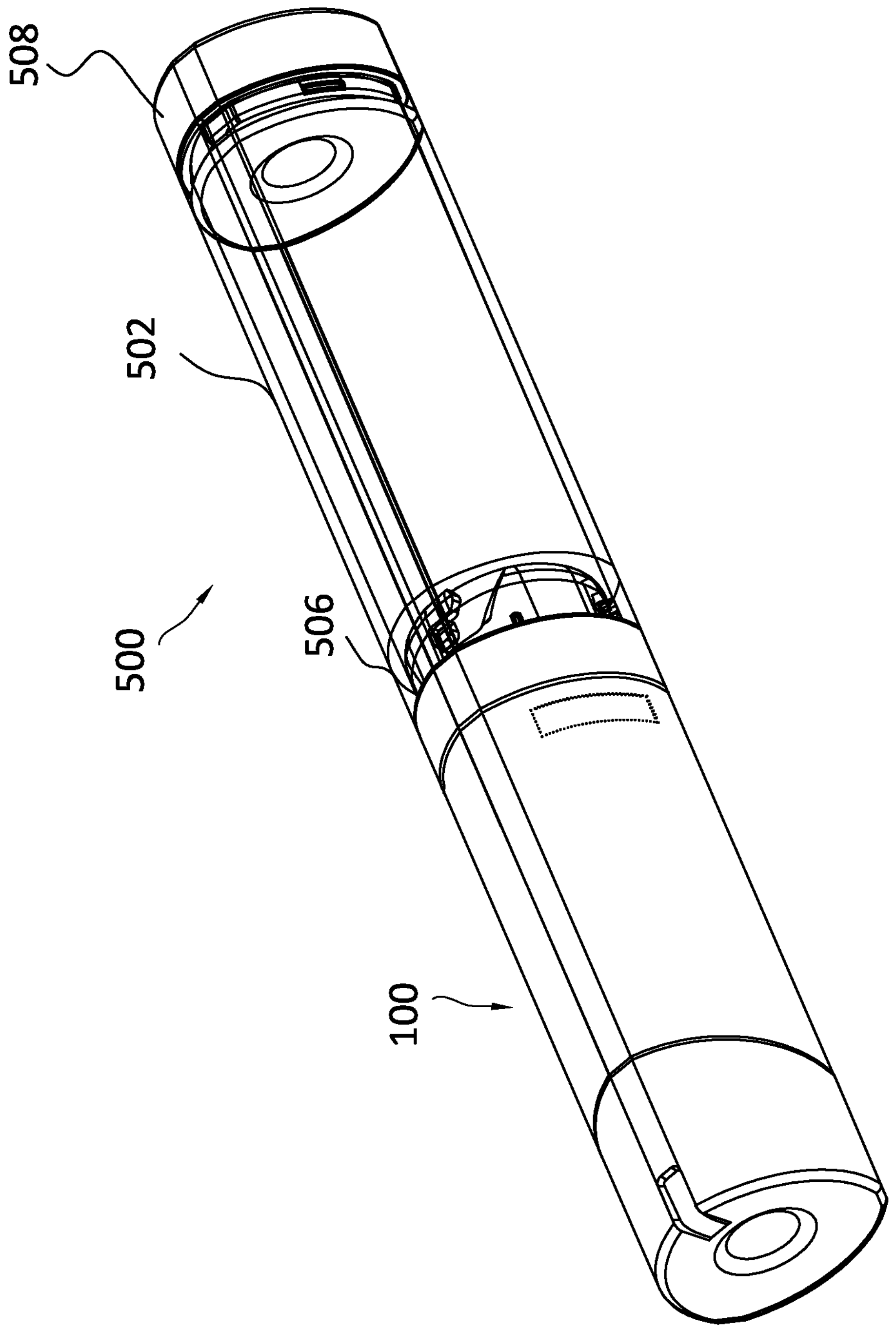

A seen in FIGS. 13A and 13B, a cap assembly 500 is configured to be removably countable to a substance storage apparatus, such as apparatus 100, or any other apparatus configured for storing at least a first portion of the substance-container 104 or the entire container 104. The cap assembly 500 comprises a housing 502 extending from the substance storage apparatus at a first end 506 to a top portion 508 at a second end. The housing defines therein a volume for storing a second portion of the substance container 104. Though in some embodiments, the entire container 104 may be enclosed within the apparatus. It is noted that in FIGS. 13A and 13B the cap assembly 500 is shown connected to the apparatus yet with the substance container 104 removed.

A connector 520 (i.e. a connecting member) is configured for removably connecting the cap assembly 500 to the substance storage apparatus, e.g. apparatus 100, 200, 400 or 550. The connector 520 may comprise a ring portion including a bayonet connector 522, snaps, tabs or any other mechanical connection means operable for selective attachment and removal of the cap assembly 500 from the apparatus before and/or after use of the container 104. In some embodiments, the connector 520 may be formed on the cap assembly 500. In some embodiments, the connector 520 may be formed on the apparatus. In some embodiments, a portion of the connector 520 may be formed on the cap assembly 500 and is configured to mate with a corresponding connector portion formed on the apparatus. In some embodiments, the connector 520 may be formed as a separate unit and may be selectively attached to any one of the cap assembly 500 and the apparatus.

The cap assembly 500 comprises a human comprehensible interaction unit 530 configured for at least one of receiving and transmitting substance-related information to a user. In some embodiments, the human comprehensible interaction unit 530 comprises a display 534 displaying to the user a time indictive of a duration which passed since a last use of the substance. The removal of the container 104 may be detected by a switch 536 and a timer module 538 and/or counter module may time the duration passed since the removal. In some embodiments the temperature detected by a temperature sensor may be displayed at display 534.

In some embodiments, the display 534 is configured to display a remaining capacity of a thermal regulation element (e.g. a PCM element 174) which is disposed within the substance storage apparatus.

In some embodiments, the display 534 is configured to display a quantity indicative of the quantity of used substance. The quantity of the substance may be provided by the user to the cap assembly 500 via a microphone 540. In some embodiments, the communication between the cap assembly 500 and the user may be via a speaker 542 and/or the microphone 540 for receiving and providing audible signals from the user and providing audible information to the user. In some embodiments, the communication between the cap assembly 500 and the user may be via optical sensors for receiving and providing optical signals from the user and providing optical information to the user.

In some embodiments, the cap assembly 500 is configured to allow the user to speak in speaker 542 to record events and amounts of substance use or other information related to the substance. In some embodiments, such events are captured when the cap assembly 500 is removed and returned to the apparatus. Such removal and return may be detected by the switch 536.

Additional components 599 may include electronics. The electronics may further include wireless communication with a mobile device 600 that allows an application running on the mobile device 600 to capture the events and optionally also activate the speaker 542 that may alert the user of events related to the substance. The electronics may also include a controller and memory and allow activation of the speaker 542 for providing audible alerts to the user regarding events that are related to the substance use (such as missed use event), even without communicating with the mobile device 600.

In some embodiments, a controller is provided for processing data received from the switch 536 and is used to detect actual use of the substance container differentiating it from accidental separation of the cap assembly 500 from the apparatus.

In some embodiments, removal of the cap assembly 500 from the apparatus is detected by the switch 536 and triggers the timer 538. Placing back the cap assembly 500 and locking or connecting it to the apparatus is detected by the switch 536 and if the time passed between these two events is at least a minimum time referred to as T(use), it is considered as a use event of the substance. T(use) can be preset by the user or be a fixed time embedded to the electronics and can be at least 60 seconds or 40 seconds, in a non-limiting example.

In some embodiments, the detection of use triggers the microphone 540 to capture a sound made by the user at any time the cap assembly 500 is removed until it is reconnected to the apparatus with the container 104 inserted in the apparatus.

In some embodiments, a controller may be provided at any one of the cap assembly 500, the apparatus or at an external location and be in wired or wireless communication with any one of the cap assembly 500 and the apparatus. The controller may be configured to analyze the sound to determine if the substance was used and how much substance was used. The controller may be configured to perform any control related or processing activity.

In some embodiments, the detection of use triggers the controller to activate the speaker 542 to ask the user to respond and a microphone 540 to capture the user response.

In some embodiments, removing the cap assembly 500 from the apparatus to remove the container therefrom and returning it after some minimum time triggers the controller to identify use of the container and display on the display 534 the time in day, (with or without full date information) relating to the use and/or activate the timer/counter module 538 to count the time from the last use.

In some embodiments in addition to displaying information relating to the time of last use, or time from last use, the external device 600 may be in communication with the cap assembly and is operable to record the event of use in an electronic format or any other format.

In some embodiments, the speaker 542 is activated following a use event and the user is asked or prompted to announce the number of used substance units. Such voice information may be analyzed by components 599 of the cap assembly 500 or communicated to the external device 600 for analyzing the voice data to provide electronic record of the amount of substance that was used.

In some embodiments, a user is provided with access to wireless earphones and/or a microphone and/or a mobile device running an application relating to the substance use, or treatment of a condition. Following substance use, the cap assembly 500 is configured to communicate with the user via his earphones or by any other means to announce the number of used substance units. This information may be recorded electronically by the application running on the mobile device and may further be communicated to a cloud server.

In some embodiments a sensor placed on the skin of the user detects the change in electrical properties of the tissue as a result of substance use, this sensor serves as an actual injection detection and further can provide information on the amount of injected substance. The data from this sensor may provided to the cap assembly 500, the apparatus and/or to the external device 600.

In some embodiments, the cap assembly 500 may be configured to be attachable to various types of substance storage apparatuses of different shapes, dimensions and functions. This facilitates adapting any one of the substance storage apparatuses to an interactive device with the user due to the human comprehensible interaction unit 530 and/or its further components.

Figure 14:
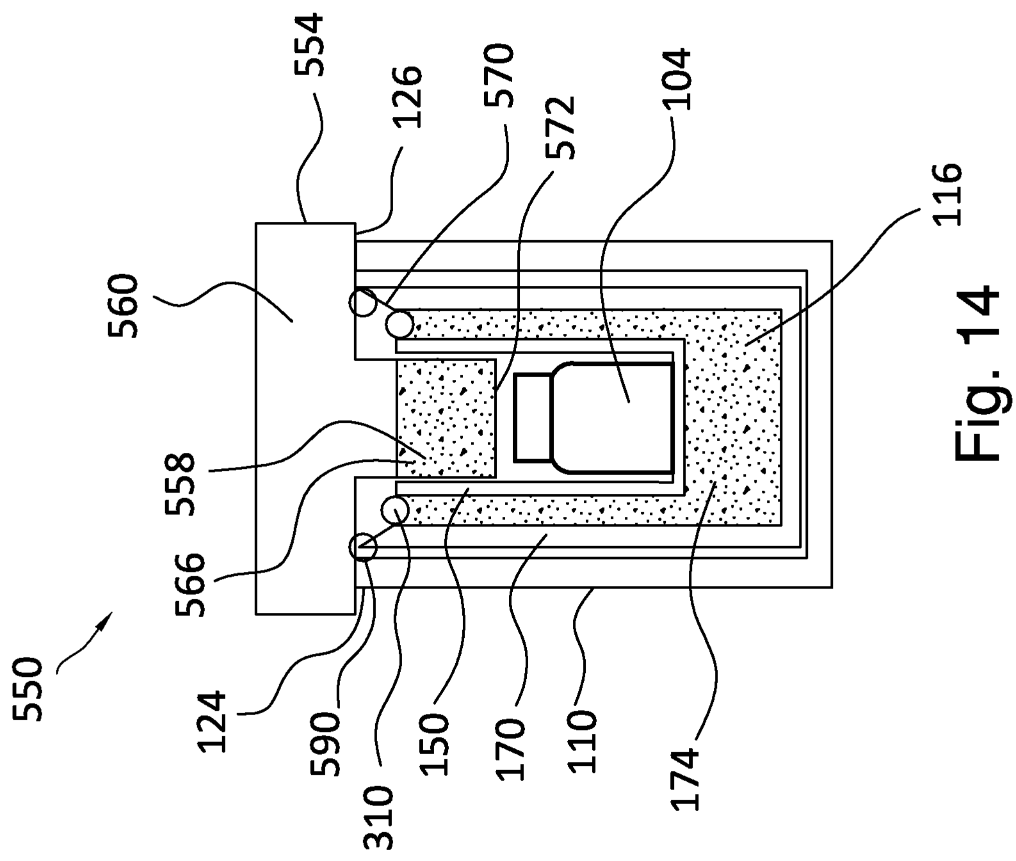
FIG. 14 is a schematic sectional illustration of an exemplary substance storage apparatus, constructed and operative according to some embodiments of the present disclosure.

As seen in FIG. 14, a substance storage apparatus 550 may be configured to fully enclose the substance-container 104, here shown comprising a vial. Apparatus 550 may comprise one or more of the features of any one of the apparatuses 100, 200 and 400, such as the thermal insulation 170 and PCM element 174.

In some embodiments, the receptacle 150 and the housing 110 may be sized and shaped so as to fully enclose the substance-container 104. The PCM element 174 is disposed in the apparatus 550 comprising a first PCM element 174. The apparatus 550 may comprise a lid 554 disposed at the proximal end 126 of the housing 110. The lid 554 is disposed at least partially over the top portion 124 of the housing 110 and comprises a second PCM element 558, which may comprise the same or a different PCM material with respect to the first PCM element 174.

In some embodiments, the lid 554 comprises a first portion 560 configured for overlaying the apparatus top portion 124 and a second portion 566 extending into the housing 110 when the lid 554 encloses the housing 110. In some embodiments, the second PCM element 558 is disposed at least within the second portion 566.

In some embodiments, as seen in FIG. 14, the thermal insulation element 170 is configured to terminate at a lip region 570 (e.g., rim 222 in FIG. 6B) in proximity to the top portion 124. The second portion 566 may be configured to extend from a container facing portion 572 and terminate generally colinearly with respect to the insulation lip region 570. In some embodiments, the second PCM element 558 is configured to axially extend into the housing towards the distal end 116, at least beyond the lip region 570.

In some embodiments, the first portion 560 comprises a thermal insulation element. In some embodiments, the first portion comprises 560 air.

In some embodiments, the lid may comprise a sealing element 590, typically disposed in proximity to the top portion 124 or any other suitable location on the lid 554.

It is noted that in reference to FIGS. 1A-14 in some embodiments, any one of the apparatuses 100, 200, 400, 550 and cap assembly 500 may be formed with an alignment mark 610 shown for example in FIG. 1A. Mark 610 is provided for guiding a user to return a removed container 104 to the same position within the apparatus as it was prior to removal from the apparatus. The mark 610 may comprise a mechanical feature, a mechanical mark, an electrical mark, an optical mark or any other suitable mark.

It is noted that in reference to FIGS. 1A-14 in some embodiments, the PCM element 174 may include a material with relatively high heat of fusion which, by melting and solidifying (namely changing its phase) at a specific phase transition temperature, is capable of absorbing, storing and releasing relatively large amounts of energy. The PCM element 174 further absorbs heat flux which may pass through the thermal insulation element 170 before it reaches the substance and/or container 104. The PCM element 174 is configured to affect the control and regulation of the environmental condition of the substance and/or container 104. The PCM element 174 may be characterized by its latent heat capacity and/or sensible heat capacity.

The PCM element 174 may be characterized by its phase transition temperature, namely the temperature wherein the first phase fully changes to the second change, such as the temperature at which the solids completely change into liquid. In some embodiments, the PCM type may be selected, inter alia, in accordance with any one of the following parameters: the required substance temperature, the time period required for maintaining the substance at the required substance temperature (or lower or higher than a predetermined temperature threshold) and the required mode (i.e. storage, typically refrigeration or use out of the refrigerator or transportation mode of the substance).

In some embodiments, the PCM element 174 may comprise an organic based PCM, an inorganic based PCM, a eutectic based PCM, or a water based PCM. Non-limiting examples of inorganic PCM comprise salt hydrates, salts, metals and alloys. Non-limiting examples of organic PCM comprise paraffin, fatty acids, oils, biocompatible oils, vegetable oils, alcohols and glycols and an oleaginous substance.

The PCM element 174 may be configured in any suitable form, such as in bulk form or microencapsulated form, for example. Microencapsulated PCMs may comprise capsules, generally with small diameters (in a non-limiting example a diameter of 1 micron to 1 centimeter). The PCM element 174 is contained within the capsule. Microencapsulation allows mixing of different PCMs with different phase transition temperatures. When the PCM is in bulk form, each type of PCM may be maintained separately by enclosing each PCM in an individual compartment, or they can be housed in the same compartment if they do not interact with each other to modify the phase temperature or latent heat capacity (latent or sensible) of either one of them.

In some embodiments, the environmental control element may comprise any suitable liquid. For a non-limiting example, the liquid may comprise water, namely an $H_2O$ containing compound at it various phases (gas, liquid, solid). In some embodiments, a first environmental control material portion may comprise the liquid and a second environmental control material portion may comprise a PCM.

In some embodiments, the PCM may be configured to remain at least partially flexible also when it is in its solid form (below its phase transition temperature) temperatures. In a non-limiting example, such a flexible PCM in a compartment may be commercially available by Glacier Tekath-ttps/glaciertek.com. These compartments contain PURE-TEMP® phase change materials commercially available from PURETEMP4232 Park Glen Road, Minneapolis, MN 55416, USA.

In some embodiments, the environmental control element may comprise a mixture of a PCM and water. The mixture may be formed in any suitable manner such as a dispersed, wet-cake type mixture or as a dispersion of microcapsules comprising PCM and water.

The substance may comprise a highest efficacy limit temperature. In some embodiments, the PCM is selected according to its transition temperature, defined as the temperature in which the PCM changes from solid to liquid phase and vice versa. The PCM is selected with a transition temperature which is at one or more (i) selected to be in the range of 0°-5° Celsius less than the substance highest efficacy limit temperature; and (ii) selected to be above room temperature. In some embodiments, the environmental control element is configured to control the at least one environmental condition without use of an external power source, thereby allowing the apparatus to be thermally self-recharging and thereby allowing the environmental control element to maintain the substance temperature below the highest efficacy limit temperature also when ambient temperatures exceed the highest efficacy limit temperature, without requiring user intervention. In other words, the environmental control element (e.g. the PCM element 174 and/or the thermal insulation element 170) is operative to control the environment condition (e.g. temperature) of the substance and/or container 104 without requiring the user to perform any activity (in a non-limiting example—the user isn't required to refrigerate the container 104 or apparatus or move the container 104 and/or apparatus from a hotter location to a colder location)

It is noted that any one of the apparatuses described herein in reference to FIGS. 1A-14 and and/or the cap assembly 500 may comprise additional components 599, such as at least one or more temperature sensors designed to monitor the temperature of the apparatus volume and/or the container 104 and/or the substance and/or the ambient environment out of the apparatus. In some embodiments, a component 599 may comprise presence sensors, designed to monitor the presence of container 104 and/or substance in the apparatus or removal therefrom. In a non-limiting example, the presence sensors may comprise an RFID tag reader or a camera, a switch or other detector, such as an optical or electronic detector for example. Exemplary additional sensors may include capacitive sensors and accelerometer sensors which may be employed to detect touch of the apparatus or removal of the container 104 from the apparatus thereby detecting presence of the container 104.

Components 599 may comprise a controller such as a processor, a power source, e.g. a battery positioned at any suitable location. Components 599 may comprise electronics, such as a thermistor, a transistor, boards, wires or circuitry and/or a control circuit for controlling electrical components of the apparatuses and/or the cap assembly 500. Electrical connections between the battery and the controller, electronics and any other electrical component, may be provided. Components 599 may comprise a memory device, and/or a timer, for example.

In some embodiments, the battery may be disposable or rechargeable.

Components 599 may comprise one or more indicators, such as LED indicators or a small electronic display, for example. The indicators may indicate one or more environmental conditions of the substance, such as the substance temperature, or any other parameter of the substance, such as color, clarity or transparency, for example.

According to some embodiments, there may be provided a control capacity indicator configured to display the remaining control capacity provided by the environmental control element (e.g. the PCM element 174) to maintain the required environmental conditions. For example, a PCM element 174 is capable of absorbing the heat flux from the ambient environment until the volume of the PCM element 174 liquidizes from a solid phase to a liquid phase. The PCM volume yet to undergo a phase change from solid to liquid is indicative of the remaining thermal control capacity of the environmental control element. The control capacity indicator may be configured as described in applicant's patent publication WO2017/090019, incorporated herein in its entirety.

Furthermore, to conserve energy of the power source, some of the components 599 may be configured to be inoperative at certain times. Upon detection of a predetermined event, such as insertion of the container 104 into the apparatus or any other event, components may be activated for a predetermined time period and shut off thereafter. In some embodiments, an accelerometer, a vibration, capacitive or movement sensor and/or the presence sensor may be used to detect the predetermined event.

In some embodiments, components 599 may comprise a camera or other optical detector or detectors array provided at any suitable location to image (or provide optical information relating to) the substance and/or container 104 and/or the apparatus and/or the cap assembly 500. The camera may transmit the images or other optical information (at visible or invisible optical wavelengths), which may be still photos or streaming images, or optical information, such as a video, either wired or wirelessly to an external device 600 (FIG. 13A).

In some embodiments, an external device 600 may be provided to receive signals or data from the apparatus and/or cap assembly 500 via a wireless transponder or any other suitable communication means, such as a wired USB connector port or any other wired or wireless connector port. The external device 600 may comprise a remote device e.g. a Smartphone, a mobile device, a computer or any device with a processor.

While the disclosure has been described with respect to a limited number of embodiment, it is to be realized that any combination of embodiments in whole or part can also be used and that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiments, it will be appreciated that many variations, modifications and other applications of the invention may be made.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Some embodiments may be distinguishable from the prior art for specifically lacking one or more features/elements/functionality (i.e., claims directed to such embodiments may include negative limitations).

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one. The phrase "and/or," as used herein in the specification and in the claims, should be understood to mean "either or both" of" the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B), in another embodiment, to B only (optionally including elements other than A), in yet another embodiment, to both A and B (optionally including other elements), etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B), in another embodiment, to at least one, optionally including more than one, B, with no A present (and optionally including elements other than A), in yet another embodiment, to at least one, optionally including more than one, A, and at least one, optionally including more than one, B (and optionally including other elements), etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A substance storage apparatus for storing a substance-container configured with an outer surface formed of a first material and for containing a substance, the apparatus comprising:

a housing formed of a base at a distal end of the storage apparatus and a lateral wall longitudinally extending therefrom to a top portion at a proximal end, the top portion comprising:

a cover, at least a portion of which is formed of a second material including a greater degree of resilience than the first material; and an aperture at least partially surrounded by the cover and configured for receiving an end of the substance-container therethrough;

a thermal insulation element disposed within the housing and configured to provide a thermal shield to the substance;

a receptacle having a size and shape configured for receiving the substance-container therein; and a phase change material (PCM) element configured to thermally regulate the temperature of the substance, wherein the PCM element is disposed within a PCM volume formed intermediate at least a section of the receptacle and at least a section of the thermal insulation element.

2. The apparatus of claim 1, wherein the cover comprises a plurality of flaps or leaflets.

3. The apparatus of claim 1, wherein the top portion further comprises at least one recess extending from the aperture.

4. The apparatus of claim 3, wherein the at least one recess comprises a plurality of recesses arranged so as to form a tricuspid valve-like shape.

5. The apparatus of claim 1, wherein:

the receptacle is formed with a peripheral wall defining therein a lumen, the lumen is configured with a predetermined diameter dimensioned to receive a reservoir region of the substance-container containing the substance therein, and the aperture is configured with a diameter either equal to or less than the predetermined lumen diameter.

6. The apparatus of claim 1, wherein the PCM element is inserted into the PCM volume in an at least partially liquid state.

7. The apparatus of claim 1, wherein the PCM element is contiguous with at least a portion of an external wall of the receptacle.

8. The apparatus of claim 6, wherein the receptacle comprises at least one lateral projection protruding from the external wall of the receptacle, the at least one lateral projection configured for positioning the receptacle within the PCM volume.

9. The apparatus of claim 8, wherein the at least one lateral projection is formed of a material with a degree of thermal conductivity equal to or greater than the degree of thermal conductivity of the PCM element.

10. The apparatus of claim 1, wherein the thermal insulation element comprises:

an external cylinder formed with an external base portion and an external peripheral wall extending longitudinally from the external base portion to a first lip thereof;

an internal cylinder formed with an internal base portion and an internal peripheral wall extending longitudinally from the internal base portion to a second lip; and a rim connecting the first lip to the second lip.

11. The apparatus of claim 1, wherein the lateral wall of the housing is formed with at least one flat surface configured to prevent rolling of the substance storage apparatus on a substantially flat surface.

12. The apparatus of claim 1, wherein the receptacle is sized and shaped so as to fully enclose the substance-container, and wherein the apparatus comprises a lid disposed at the proximal end of the housing.

13. The apparatus of claim 1, wherein the receptacle is configured with a length along its longitudinal axis dimensioned to receive a needle-containing region and a substance reservoir region of a substance-injection device of the substance-container which constitutes the substance-injection device configured with the substance reservoir region disposed along a longitudinal axis thereof, intermediate to a plunger region positioned at a first end thereof, and the needle-containing region positioned at a second end thereof, and wherein at least a portion of the plunger region protrudes from the top portion of the housing.

14. The apparatus of claim 13, wherein the receptacle is shaped complementary to the shape of the substance-injection device, and comprises:

a reservoir region-receiving portion configured with a first receptacle-portion having a first diameter and being dimensioned to receive the reservoir region of the substance-injection device; and a needle-containing region-receiving portion configured with a second receptacle portion including a second diameter and being dimensioned to receive the needle-containing region of the substance-injection device, wherein the second diameter of the second receptacle portion is smaller than the first diameter of the first receptacle portion, thereby the receptacle is shaped complementary to the shape of the substance-injection device which is formed with:

a first container portion substantially perpendicular to the longitudinal axis and disposed at the reservoir region, the first container portion configured with a corresponding first diameter; and a second container portion substantially parallel to the first container portion and disposed at the needle-containing region, the second container portion configured with a corresponding second diameter smaller than the first device diameter.

15. The apparatus of claim 14, wherein the receptacle comprises:

the reservoir region-receiving portion dimensioned to snugly receive the reservoir region; and the needle-containing region-receiving portion dimensioned to snugly receive the needle-containing region.

16. The apparatus of claim 14, wherein the receptacle is formed with a protuberance protruding from an internal surface of the receptacle at the reservoir receiving-portion, the protuberance being configured for housing a temperature sensor and positioning the temperature sensor to face the substance reservoir region.

17. The apparatus of claim 1, wherein the housing is formed with at least one retainer for preventing the receptacle from being axially displaced in response to expansion of the PCM element within the PCM volume when in an at least partial liquid state.

18. A substance storage apparatus for storing a substance-container configured with a peripheral wall and for containing a substance, the apparatus comprising:

a housing formed of a base portion at a distal end of the storage apparatus and a lateral wall longitudinally extending therefrom to a top portion at a proximal end of the apparatus, a thermal insulation element disposed within the housing and being configured to provide a thermal shield to the substance;

a receptacle configured for receiving the substance-container therein;

a first phase change material (PCM) element configured to thermally regulate the temperature of the substance, wherein the first PCM element is disposed within a PCM volume formed intermediate the receptacle and the thermal insulation element; and a lid disposed at least partially over the top portion of the housing and comprising a second PCM element.

19. The apparatus of claim 18, wherein the lid comprises a first portion configured for overlaying the top portion and a second portion extending into the housing when the lid encloses the housing.

20. The apparatus of claim 18, wherein the thermal insulation element of the housing terminates at a lip region thereof, and the second PCM element contained in the second portion is configured to axially extend into the housing towards the distal end, at least beyond the lip region.

21. A substance storage apparatus for storing a substance-container configured with an outer surface formed of a first material and for containing a substance, the apparatus comprising:

a housing formed of a base at a distal end of the storage apparatus and a lateral wall longitudinally extending therefrom to a top portion at a proximal end, the top portion comprising:

a cover and an aperture at least partially surrounded by the cover and configured for receiving an end of the substance-container therethrough, wherein at least a portion of the cover is formed of a resilient material capable of being elastically deformed upon insertion of the substance-container through the aperture and capable of substantially rebounding to its original shape after deformation, such that the at least a portion of the cover is operable to expand to accommodate insertion of the substance-container and to contract to grip the outer surface of the substance-container so as to secure the substance-container within the housing;

a thermal insulation element disposed within the housing and configured to provide a thermal shield to the substance;

a receptacle having a size and shape configured for receiving the substance-container therein; and a phase change material (PCM) element configured to thermally regulate the temperature of the substance.

* * * * *